United States Patent
Yamanaka et al.

(10) Patent No.: US 10,640,462 B2
(45) Date of Patent: May 5, 2020

(54) OIL GELATOR

(71) Applicants: NATIONAL UNIVERSITY CORPORATION SHIZUOKA UNIVERSITY, Shizuoka-Shi, Shizuoka (JP); NISSAN CHEMICAL INDUSTRIES, LTD., Tokyo (JP)

(72) Inventors: Masamichi Yamanaka, Shizuoka (JP); Nobuhide Miyachi, Tokyo (JP)

(73) Assignees: NATIONAL UNIVERSITY CORPORATION SHIZUOKA UNIVERSITY, Shizuoka (JP); NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 16/061,198

(22) PCT Filed: Dec. 9, 2016

(86) PCT No.: PCT/JP2016/086770
§ 371 (c)(1),
(2) Date: Jun. 11, 2018

(87) PCT Pub. No.: WO2017/099232
PCT Pub. Date: Jun. 15, 2017

(65) Prior Publication Data
US 2018/0362454 A1    Dec. 20, 2018

(30) Foreign Application Priority Data

Dec. 11, 2015 (JP) .................... 2015-242397

(51) Int. Cl.
*C07C 275/28* (2006.01)
*C09K 3/00* (2006.01)
(Continued)

(52) U.S. Cl.
CPC ........... *C07C 275/30* (2013.01); *A61K 8/42* (2013.01); *A61K 47/16* (2013.01); *C07C 275/28* (2013.01); *C07C 275/36* (2013.01); *C09K 3/00* (2013.01)

(58) Field of Classification Search
None
See application file for complete search history.

(56) References Cited

U.S. PATENT DOCUMENTS 3,211,692 A * 10/1965 Hopkins ........... C07C 273/1827
524/216
5,059,002 A * 10/1991 Francis ................. C07C 271/28
359/241

FOREIGN PATENT DOCUMENTS

CN    1271725 A     11/2000
CN   102503860 A    6/2012
(Continued)

OTHER PUBLICATIONS

Piana ("Substituent interference on supramolecular assembly in urea gelators: synthesis, structure prediction and NMR" Soft Matter, 2016 (published online Mar. 29, 2016), 12, p. 4034-4043) (Year: 2016).*

(Continued)

*Primary Examiner* — Amy C Bonaparte
(74) *Attorney, Agent, or Firm* — Oliff PLC

(57) ABSTRACT

There is provided a novel gelator containing a monourea derivative. A gelator comprising a compound of formula (1):

[1]

(Continued)

wherein $R^1$ is a linear or branched alkyl group having a carbon atom number of 2 to 20, a cyclic alkyl group having a carbon atom number of 3 to 20, or a linear or branched alkenyl group having a carbon atom number of 12 to 20; and Ar is a $C_{6-18}$ aryl group unsubstituted or optionally substituted with at least one substituent selected from the group consisting of a $C_{1-10}$ alkyl group, a $C_{1-10}$ alkoxy group, a $C_{6-18}$ aryloxy group, a halogen atom, a nitro group, a phenyl group, a $C_{2-10}$ alkylcarbonyl group, and a $C_{7-18}$ aralkyl group.

6 Claims, 7 Drawing Sheets

(51) Int. Cl.
*A61K 47/16* (2006.01)
*A61K 8/42* (2006.01)
*C07C 275/30* (2006.01)
*C07C 275/36* (2006.01)

(56) References Cited

FOREIGN PATENT DOCUMENTS

| CN | 102993075 A | 3/2013 |
|---|---|---|
| CN | 103664704 A | 3/2014 |
| GB | 1028818 A | 5/1966 |
| JP | S50-030801 A | 3/1975 |
| JP | H11-349553 A | 12/1999 |
| JP | 2001-131014 A | 5/2001 |
| JP | 2005-028692 A | 2/2005 |
| JP | 2006-511484 A | 4/2006 |
| JP | 2009-221266 A | 10/2009 |
| JP | 2013-151628 A | 8/2013 |
| WO | 2009/077844 A2 | 6/2009 |
| WO | 2013/133419 A1 | 9/2013 |
| WO | 2015/136292 A1 | 9/2015 |

OTHER PUBLICATIONS

Li ("A Functional Proteomic Strategy to Discover Inhibitors for Uncharacterized Hydrolases" J. Am. Chem. Soc. 2007, 129, p. 9594-9595, including Supporting Information p. S1-S23) (Year: 2007).*
Schenach ("The Bacteriostatic Effectiveness of 1-Alkyl-3-(3,4-dichlorophenyl)ureas" J. Med. Chem. 1966, 9(3), p. 426-428) (Year: 1966).*
Lombardino ("Preparation and Hypoglycemic Activity of Some 3,5-Disubstituted Hydantoins" J. Med. Chem. 1964, 7(1), p. 97-101) (Year: 1964).*
S. Shinkai et al., "Sugar-Integrated Gelators of Organic Solvents", Chem. Eur. J., vol. 7, No. 20, pp. 4327-4334, 2001.
P. Xing et. al., "Utilizing dual responsive supramolecular gel to stabilize graphene oxide in apolar solvents", Colloid and Polymer Science, pp. 3223-3231, 2014.
Roark et. al., "Inhibitors of Acyl-CoA:Cholesterol Acyltransferase (ACAT). 2. Modification of Fatty Acid Anilide ACAT Inhibitors: Bioisosteric Replacement of the Amide Bond", J. Med. Chem., pp. 1662-1668, 1993.
Feb. 7, 2017 International Search Report issued in International Patent Application No. PCT/JP2016/086770.

\* cited by examiner

OIL GELATOR

TECHNICAL FIELD

The present invention relates to a novel gelator, and specifically relates to a novel gelator containing a monourea derivative that can form a gel with an organic liquid other than water.

BACKGROUND ART

A structure containing a fluid within a three-dimensional network structure, which is formed using a substance with a gel-forming ability (hereinafter, a "gelator"), is referred to as a gel. In general, when the fluid is water, the gel is referred to as a hydrogel, and when the fluid is an organic liquid other than water (such as an organic solvent or an oil), the gel is referred to as an organogel or an oil gel. Oil gels (organogels) are used in the fields of cosmetics, pharmaceuticals, agrochemicals, foods, adhesives, coating materials, resins, and the like, to adjust the flowability of cosmetics or coating materials. Oil gels are also extensively used in the fields of environmental conservation to prevent water pollution by gelation of waste oil to form solids, for example.

While research on gelators has mainly focused on polymer compounds, research and development has recently been in progress on low-molecular-weight compounds that can be more readily provided with a variety of functions than polymer compounds. In the past, various compounds have been proposed as low-molecular-weight gelators that can form highly stable gels with various organic solvents even when they are added in small amounts. By way of example, reports have been made on gelators obtained using saccharide derivatives derived from various monosaccharides (Non-Patent Document 1 and Patent Document 1) and gelators formed of alkyl hydrazide compounds (Patent Document 2).

PRIOR ART DOCUMENTS

Patent Documents

Patent Document 1: WO 2013/133419
Patent Document 2: Japanese Patent Application Publication No. 2013-151628 (JP 2013-151628 A)

Non-Patent Document

Non-Patent Document 1: S. Shinkai et al., Chem. Eur. J. 2001, 7, No 20, 4327-4334

SUMMARY OF THE INVENTION

Problem to be Solved by the Invention

As described above, oil gels (organogels) are used in extensive fields, and the fields of application thereof are expected to expand in the future.

An object of the present invention is to provide a novel gelator having a heretofore-unproposed structure, particularly a novel gelator that can form an oil gel.

Means for Solving the Problem

As a result of diligent study to solve the aforementioned problem, the inventors of the present invention have surprisingly found that when a monourea derivative is used as a gelator, it can form gels with various solvents, thus completing the present invention.

In summary, a first aspect of the present invention relates to a gelator comprising a compound of formula (1):

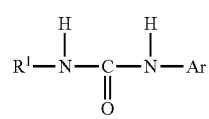

[1]

(wherein $R^1$ is a linear or branched alkyl group having a carbon atom number of 2 to 20, a cyclic alkyl group having a carbon atom number of 3 to 20, or a linear or branched alkenyl group having a carbon atom number of 12 to 20; and Ar is a $C_{6-18}$ aryl group unsubstituted or optionally substituted with at least one substituent selected from the group consisting of a $C_{1-10}$ alkyl group, a $C_{1-10}$ alkoxy group, a $C_{6-18}$ aryloxy group, a halogen atom, a nitro group, a phenyl group, a $C_{2-10}$ alkylcarbonyl group, and a $C_{7-18}$ aralkyl group).

A second aspect of the present invention relates to the gelator according to the first aspect, wherein $R^1$ is a linear or branched alkyl group having a carbon atom number of 12 to 20, a cyclic alkyl group having a carbon atom number of 12 to 20, or a linear or branched alkenyl group having a carbon atom number of 12 to 20.

A third aspect of the present invention relates to the gelator according to the first or second aspect, wherein $R^1$ is a linear alkyl group having a carbon atom number of 14 to 20, and Ar is a phenyl group unsubstituted or optionally substituted with at least one substituent selected from the group consisting of a $C_{1-10}$ alkyl group, a halogen atom, and a $C_{7-18}$ aralkyl group.

A fourth aspect of the present invention relates to the gelator according to any one of the first to third aspects, wherein Ar is a phenyl group substituted with a benzyl group.

A fifth aspect of the present invention relates to a gel comprising the gelator according to any one of the first to fourth aspects, and a hydrophobic organic solvent, a hydrophilic organic solution, or an ionic liquid.

A sixth aspect of the present invention relates to the gel according to the fifth aspect, wherein the hydrophobic organic solvent is at least one selected from the group consisting of a vegetable oil, an ester, a silicone oil, and a hydrocarbon.

A seventh aspect of the present invention relates to the gel according to the fifth aspect, wherein the hydrophilic organic solvent is at least one selected from the group consisting of methanol, ethanol, 2-propanol, i-butanol, pentanol, hexanol, 1-octanol, isooctanol, acetone, cyclohexanone, acetonitrile, dioxane, glycerol, butanediol, propylene glycol, ethylene glycol, and dimethylsulfoxide.

An eighth aspect of the present invention relates to the gel according to the fifth aspect, wherein the hydrophilic organic solution is a mixed solvent of a hydrophilic organic solvent and water, and the hydrophilic organic solvent is at least one selected from the group consisting of methanol, ethanol, 2-propanol, i-butanol, pentanol, hexanol, 1-octanol, isooctanol, acetone, cyclohexanone, acetonitrile, dioxane, glycerol, butanediol, propylene glycol, ethylene glycol, and dimethylsulfoxide.

A ninth aspect of the present invention relates to the gel according to the fifth aspect, wherein the ionic liquid comprises a combination of a cationic species selected from the group consisting of imidazolium, pyridinium, piperidinium, pyrrolidinium, phosphonium, ammonium, and sulfonium, and an anionic species selected from the group consisting of a halogen, a carboxylate, a sulfate, a sulfonate, a thiocyanate, a nitrate, an aluminate, a borate, a phosphate, an amide, an antimonate, an imide, and a methide.

A tenth aspect of the present invention relates to a compound of formula (1):

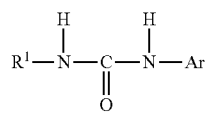

[1]

(wherein $R^1$ is a linear or branched alkyl group having a carbon atom number of 2 to 20, a cyclic alkyl group having a carbon atom number of 3 to 20, or a linear or branched alkenyl group having a carbon atom number of 12 to 20; and Ar is a $C_{6-18}$ aryl group unsubstituted or optionally substituted with at least one substituent selected from the group consisting of a $C_{1-10}$ alkyl group, a $C_{1-10}$ alkoxy group, a $C_{6-18}$ aryloxy group, a halogen atom, a nitro group, a phenyl group, a $C_{2-10}$ alkylcarbonyl group, and a $C_{7-18}$ aralkyl group).

An eleventh aspect of the present invention relates to the compound according to the tenth aspect, wherein $R^1$ is a linear or branched alkyl group having a carbon atom number of 12 to 20, a cyclic alkyl group having a carbon atom number of 12 to 20, or a linear or branched alkenyl group having a carbon atom number of 12 to 20.

A twelfth aspect of the present invention relates to the compound according to the tenth or eleventh aspect, wherein Ar is a phenyl group unsubstituted or substituted with at least one substituent selected from the group consisting of a $C_{1-5}$ alkyl group, a chloro group, a bromo group, a nitro group, a $C_{2-10}$ alkylcarbonyl group, and a $C_{7-10}$ aralkyl group.

Effects of the Invention

The gelator of the present invention can form gels by gelation of organic solvents and the like.

In particular, the gelator of the present invention can form gels with various media such as a hydrophobic organic solvent, a hydrophilic organic solution, and an ionic liquid, and can readily provide gels containing these media.

MODES FOR CARRYING OUT THE INVENTION

[Gelator]

Figure 1:
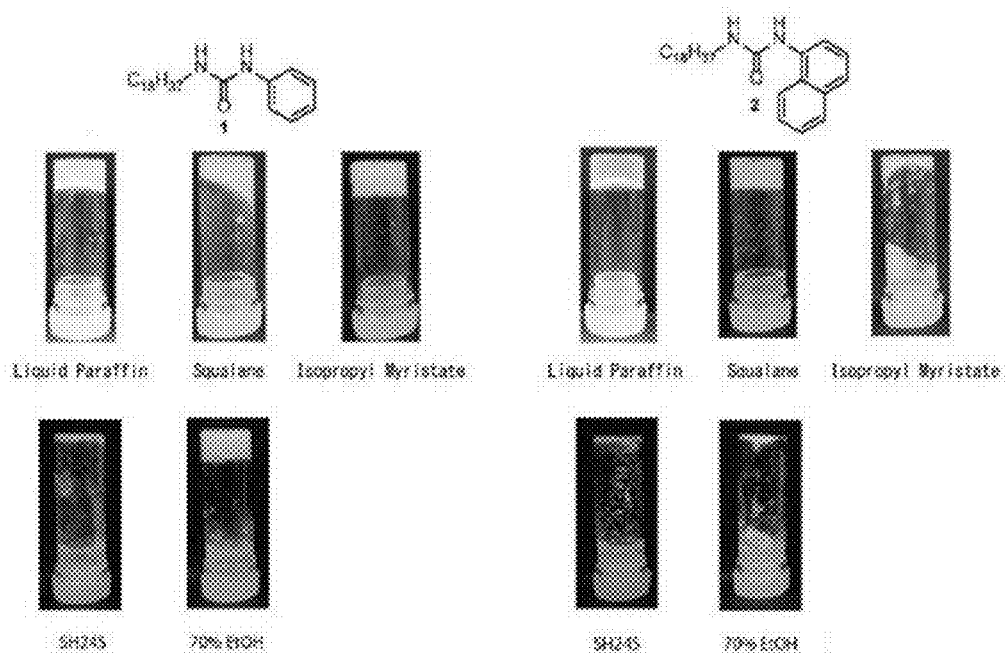
FIG. 1 is a photograph showing gelation behavior of a compound of formula 1 or 2 in various media (liquid paraffin, squalane, isopropyl myristate, SH245, and 70% EtOH) in Example 2.
Figure 2:
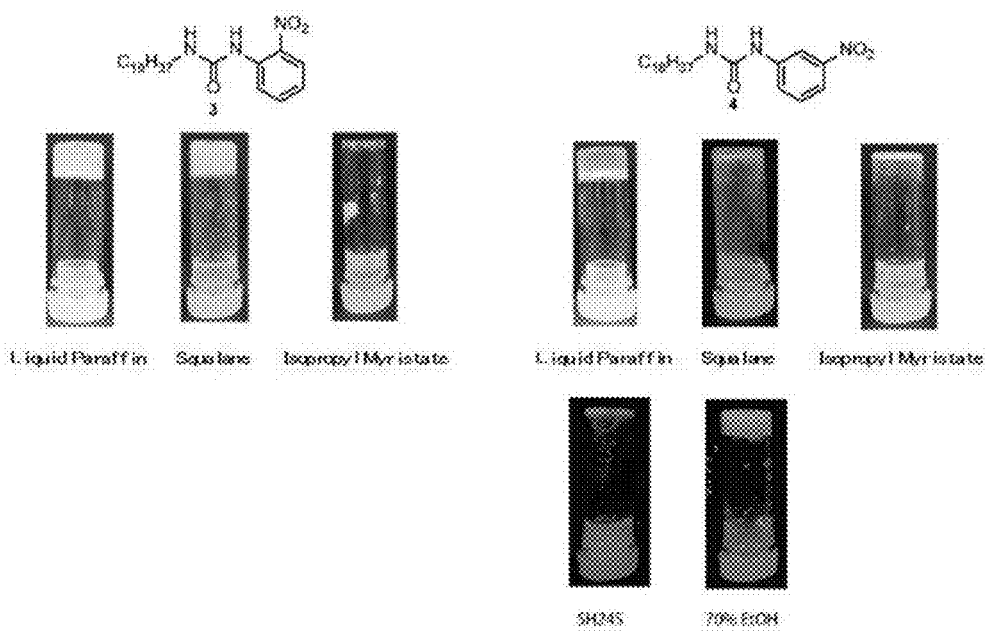
FIG. 2 is a photograph showing gelation behavior of a compound of formula 3 or 4 in various media (liquid paraffin, squalane, isopropyl myristate, SH245, and 70% EtOH) in Example 2.
Figure 3:
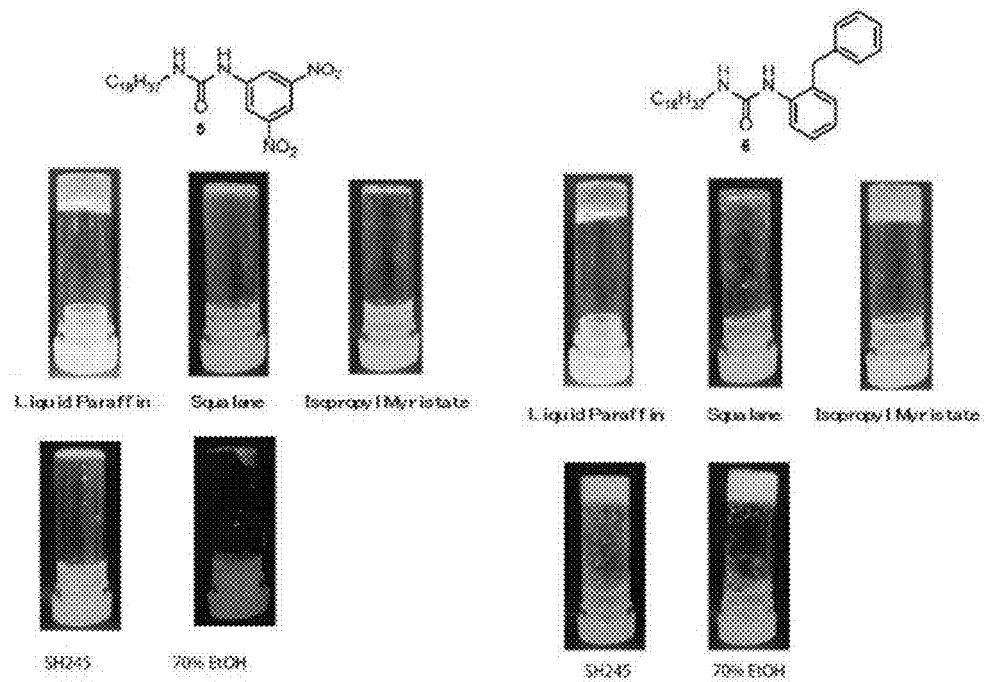
FIG. 3 is a photograph showing gelation behavior of a compound of formula 5 or 6 in various media (liquid paraffin, squalane, isopropyl myristate, SH245, and 70% EtOH) in Example 2.
Figure 4:
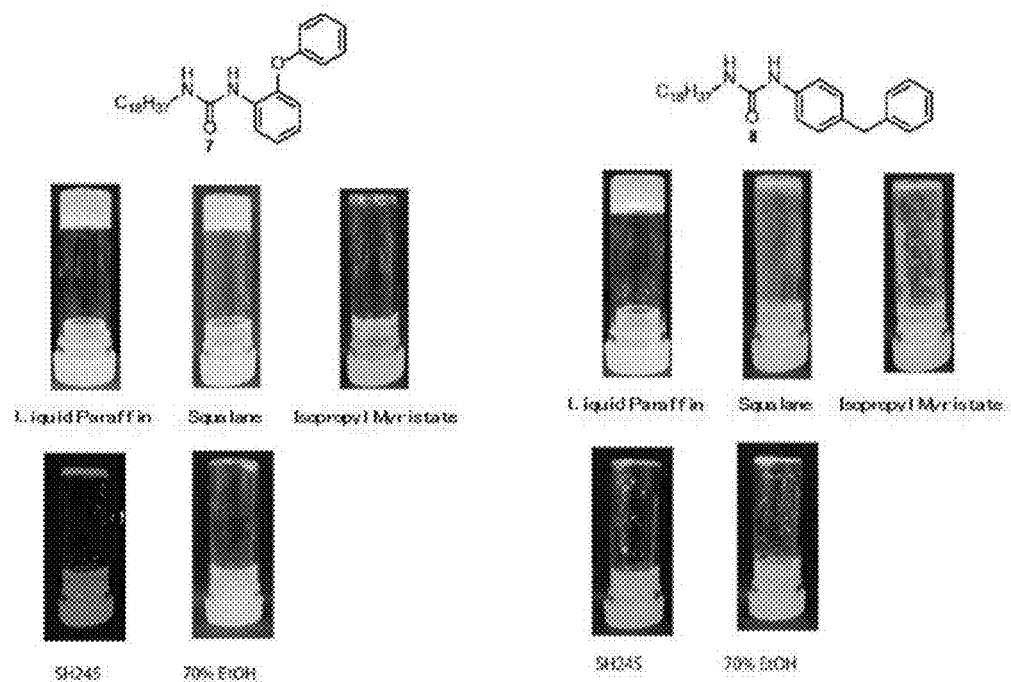
FIG. 4 is a photograph showing gelation behavior of a compound of formula 7 or 8 in various media (liquid paraffin, squalane, isopropyl myristate, SH245, and 70% EtOH) in Example 2.
Figure 5:
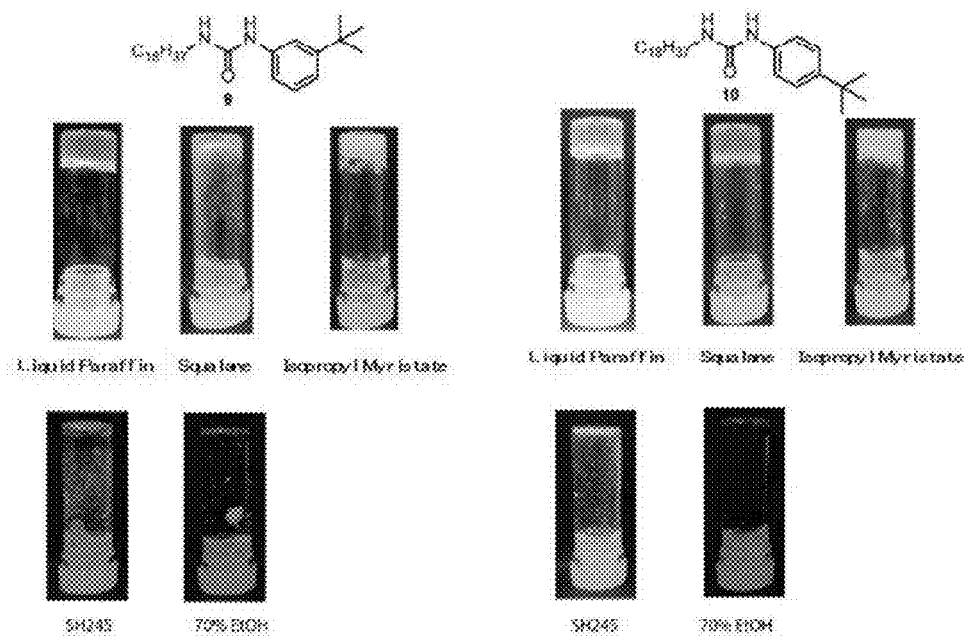
FIG. 5 is a photograph showing gelation behavior of a compound of formula 9 or 10 in various media (liquid paraffin, squalane, isopropyl myristate, SH245, and 70% EtOH) in Example 2.
Figure 6:
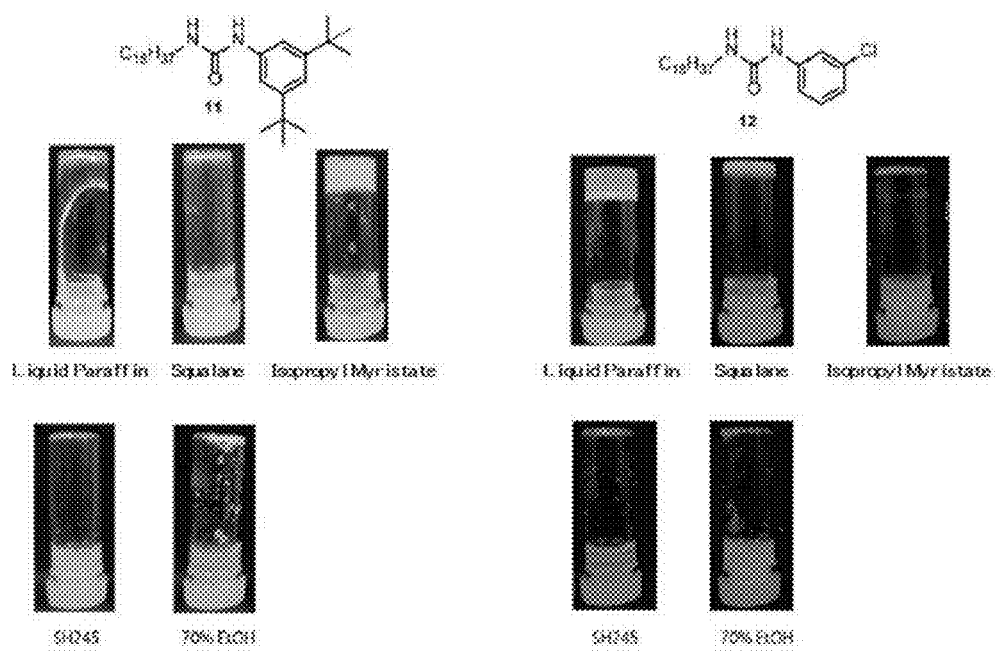
FIG. 6 is a photograph showing gelation behavior of a compound of formula 11 or 12 in various media (liquid paraffin, squalane, isopropyl myristate, SH245, and 70% EtOH) in Example 2.
Figure 7:
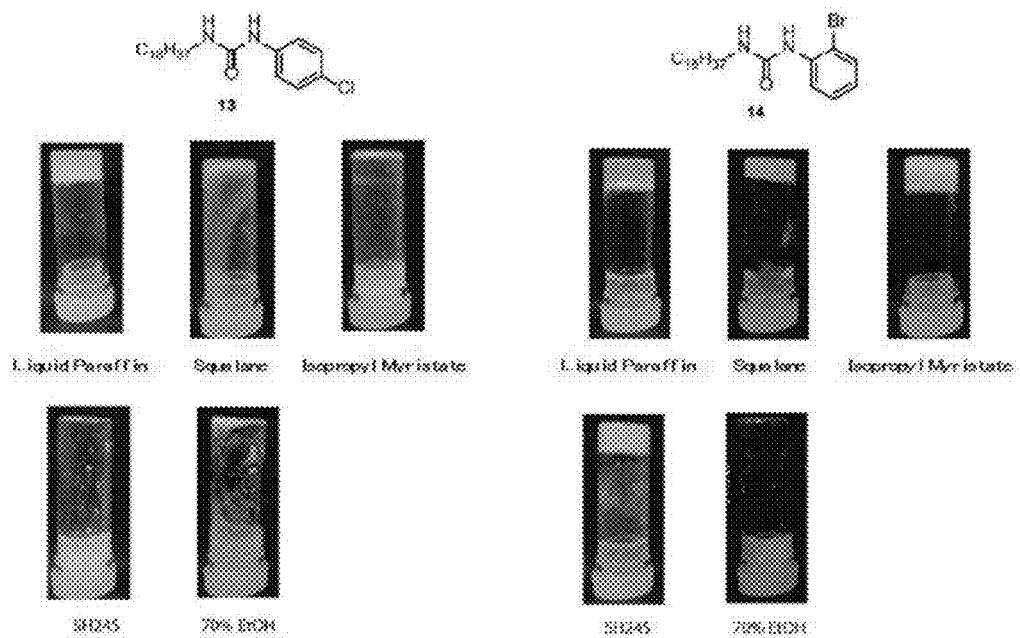
FIG. 7 is a photograph showing gelation behavior of a compound of formula 13 or 14 in various media (liquid paraffin, squalane, isopropyl myristate, SH245, and 70% EtOH) in Example 2.
Figure 8:
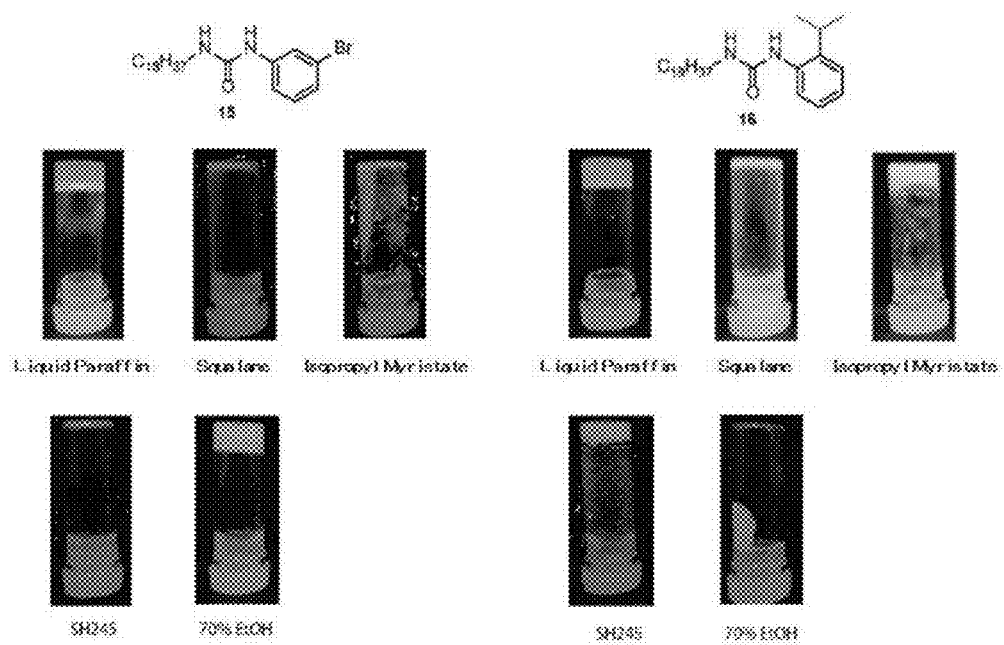
FIG. 8 is a photograph showing gelation behavior of a compound of formula 15 or 16 in various media (liquid paraffin, squalane, isopropyl myristate, SH245, and 70% EtOH) in Example 2.
Figure 9:
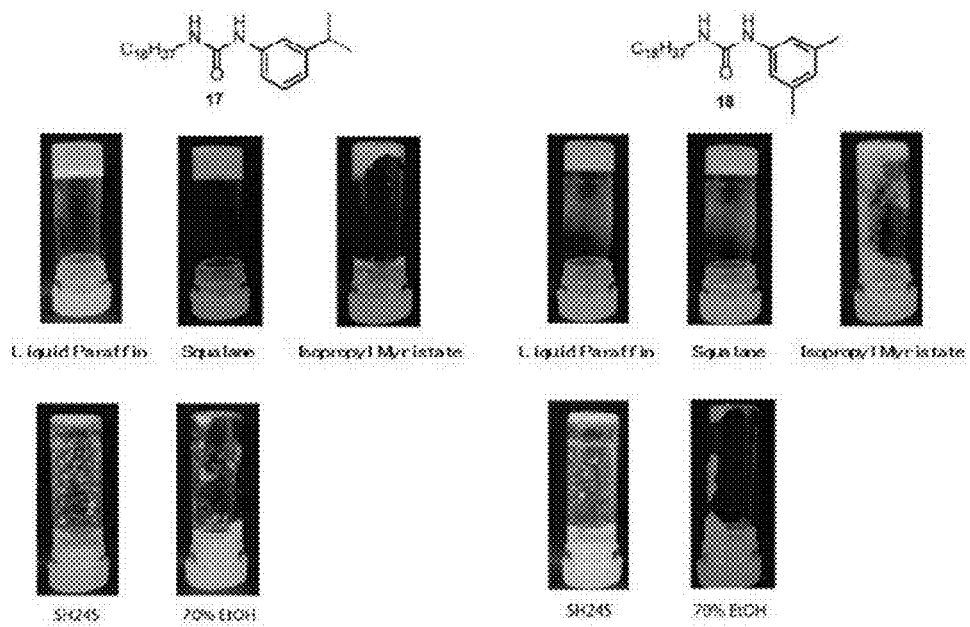
FIG. 9 is a photograph showing gelation behavior of a compound of formula 17 or 18 in various media (liquid paraffin, squalane, isopropyl myristate, SH245, and 70% EtOH) in Example 2.

A gelator of the present invention comprises a monourea compound of formula [1]:

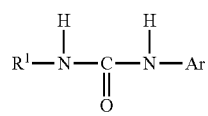

[1]

(wherein $R^1$ is a linear or branched alkyl group having a carbon atom number of 2 to 20, a cyclic alkyl group having a carbon atom number of 3 to 20, or a linear or branched alkenyl group having a carbon atom number of 12 to 20; and Ar is a $C_{6-18}$ aryl group unsubstituted or optionally substituted with at least one substituent selected from the group consisting of a $C_{1-10}$ alkyl group, a $C_{1-10}$ alkoxy group, a $C_{6-18}$ aryloxy group, a halogen atom, a nitro group, a phenyl group, a $C_{2-10}$ alkylcarbonyl group, and a $C_{7-18}$ aralkyl group).

Examples of the linear or branched alkyl group having a carbon atom number of 2 to 20 of $R^1$ include ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, and eicosyl group, as well as branched groups thereof.

Examples of the cyclic alkyl group having a carbon atom number of 3 to 20 include not only groups consisting only of cyclic alkyl groups (for example, cyclopropyl group, cyclobutyl group, cyclopentyl group, cyclohexyl group, cycloheptyl group, cyclooctyl group, cyclononyl group, cyclodecyl group, cycloundecyl group, cyclododecyl group, cyclotridecyl group, cyclotetradecyl group, cyclopentadecyl group, cyclohexadecyl group, cyc loheptadecyl group, cyclooctadecyl group, cyclononadecyl group, and cycloeicosyl group), but also linear and/or branched alkyl groups having cyclic structures such as a cyclopentyl ring and a cyclohexyl ring, and having a carbon atom number of 3 to 20.

Examples of the linear or branched alkenyl group having a carbon atom number of 12 to 20 include dodecenyl group, tridecenyl group, tetradecenyl group, pentadecenyl group, hexadecenyl group, heptadecenyl group, octadecenyl group, nonadecenyl group, and eicosenyl group, as well as branched groups thereof.

Examples of the $C_{6-18}$ aryl group of Ar include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, and 9-phenanthryl group.

Examples of the $C_{1-10}$ alkyl group as a substituent of Ar include linear, branched, or cyclic alkyl groups, including methyl group, ethyl group, n-propyl group, i-propyl group, cyclopropyl group, n-butyl group, i-butyl group, s-butyl group, t-butyl group, cyclobutyl group, 1-methyl-cyclopropyl group, 2-methyl-cyclopropyl group, n-pentyl group, 1-methyl-n-butyl group, 2-methyl-n-butyl group, 3-methyl-n-butyl group, 1,1-dimethyl-n-propyl group, 1,2-dimethyl-n-propyl group, 2,2-dimethyl-n-propyl group, 1-ethyl-n-propyl group, cyclopentyl group, 1-methyl-cyclobutyl group, 2-methyl-cyclobutyl group, 3-methyl-cyclobutyl group, 1,2-dimethyl-cyclopropyl group, 2,3-dimethyl-cyclopropyl group, 1-ethyl-cyclopropyl group, 2-ethyl-cyclopropyl group, n-hexyl group, 1-methyl-n-pentyl group, 2-methyl-n-pentyl group, 3-methyl-n-pentyl group, 4-methyl-n-pentyl group, 1,1-dimethyl-n-butyl group, 1,2-dimethyl-n-butyl group, 1,3-dimethyl-n-butyl group, 2,2-dimethyl-n-butyl group, 2,3-dimethyl-n-butyl group, 3,3-dimethyl-n-butyl group, 1-ethyl-n-butyl group, 2-ethyl-n-butyl group, 1,1,2-trimethyl-n-propyl group, 1,2,2-trimethyl-n-propyl group, 1-ethyl-1-methyl-n-propyl group, 1-ethyl-2-methyl-n-propyl group, cyclohexyl group, 1-methyl-cyclopentyl group, 2-methyl-cyclopentyl group, 3-methyl-cyclopentyl group, 1-ethyl-cyclobutyl group, 2-ethyl-cyclobutyl group, 3-ethyl-cyclobutyl group, 1,2-dimethyl-cyclobutyl group, 1,3-dimethyl-cyclobutyl group, 2,2-dimethyl-cyclobutyl group, 2,3-dimethyl-cyclobutyl group, 2,4-dimethyl-cyclobutyl group, 3,3-dimethyl-cyclobutyl group, 1-n-propyl-cyclopropyl group, 2-n-propyl-cyclopropyl group, 1-i-propyl-cyclopropyl group, 2-i-propyl-cyclopropyl group, 1,2,2-trimethyl-cyclopropyl group, 1,2,3-trimethyl-cyclopropyl group, 2,2,3-trimethyl-cyclopropyl group, 1-ethyl-2-methyl-cyclopropyl group, 2-ethyl-l-methyl-cyclopropyl group, 2-ethyl-2-methyl-cyclopropyl group, 2-ethyl-3-methyl-cyclopropyl group, n-heptyl group, n-octyl group, 2-ethylhexyl group, n-nonyl group, and n-decyl group.

Examples of the $C_{1-10}$ alkoxy group include groups in which the above-mentioned alkyl groups are attached to oxygen, including methoxy group, ethoxy group, n-propoxy group, i-propoxy group, n-butoxy group, i-butoxy group, s-butoxy group, t-butoxy group, n-pentoxy group, 1-methyl-n-butoxy group, 2-methyl-n-butoxy group, 3-methyl-n-butoxy group, 1,1-dimethyl-n-propoxy group, 1,2-dimethyl-n-propoxy group, 2,2-dimethyl-n-propoxy group, 1-ethyl-n-propoxy group, n-hexyloxy group, 1-methyl-n-pentyloxy group, 2-methyl-n-pentyloxy group, 3-methyl-n-pentyloxy group, 4-methyl-n-pentyloxy group, 1,1-dimethyl-n-butoxy group, 1,2-dimethyl-n-butoxy group, 1,3-dimethyl-n-butoxy group, 2,2-dimethyl-n-butoxy group, 2,3-dimethyl-n-butoxy group, 3,3-dimethyl-n-butoxy group, 1-ethyl-n-butoxy group, 2-ethyl-n-butoxy group, 1,1,2-trimethyl-n-propoxy group, 1,2,2-trimethyl-n-propoxy group, 1-ethyl-l-methyl-n-propoxy group, and 1-ethyl-2-methyl-n-propoxy group.

Examples of the $C_{6-18}$ aryloxy group include groups in which the above-mentioned aryl groups are attached to oxygen, including phenyloxy group (phenoxy group), α-naphthyloxy group, β-naphthyloxy group, 1-anthryloxy group, 2-anthryloxy group, 9-anthryloxy group, 1-phenanthryloxy group, 2-phenanthryloxy group, 3-phenanthryloxy group, 4-phenanthryloxy group, and 9-phenanthryloxy group.

Examples of the halogen atom include a chlorine atom, a bromine atom, and an iodine atom.

Examples of the $C_{2-10}$ alkylcarbonyl group include groups in which the above-mentioned alkyl groups are attached to carbonyl group, including methylcarbonyl group, ethylcarbonyl group, n-propylcarbonyl group, i-propylcarbonyl group, cyclopropylcarbonyl group, n-butylcarbonyl group, i-butylcarbonyl group, s-butylcarbonyl group, t-butylcarbonyl group, cyclobutylcarbonyl group, 1-methyl-cyclopropylcarbonyl group, 2-methyl-cyclopropylcarbonyl group, n-pentylcarbonyl group, 1-methyl-n-butylcarbonyl group, 2-methyl-n-butylcarbonyl group, 3-methyl-n-butylcarbonyl group, 1,1-dimethyl-n-propylcarbonyl group, 1,2-dimethyl-n-propylcarbonyl group, 2,2-dimethyl-n-propylcarbonyl group, 1-ethyl-n-propylcarbonyl group, cyclopentylcarbonyl group, 1-methyl-cyclobutylcarbonyl group, 2-methyl-cyclobutylcarbonyl group, 3-methyl-cyclobutylcarbonyl group, 1,2-dimethyl-cyclopropylcarbonyl group, 2,3-dimethyl-cyclopropylcarbonyl group, 1-ethyl-cyclopropylcarbonyl group, 2-ethyl-cyclopropylcarbonyl group, n-hexylcarbonyl group, 1-methyl-n-pentylcarbonyl group, 2-methyl-n-pentylcarbonyl group, 3-methyl-n-pentylcarbonyl group, 4-methyl-n-pentylcarbonyl group, 1,1-dimethyl-n-butylcarbonyl group, 1,2-dimethyl-n-butylcarbonyl group, 1,3-dimethyl-n-butylcarbonyl group, 2,2-dimethyl-n-butylcarbonyl group, 2,3-dimethyl-n-butylcarbonyl group, 3,3-dimethyl-n-butylcarbonyl group, 1-ethyl-n-butylcarbonyl group, 2-ethyl-n-butylcarbonyl group, 1,1,2-trimethyl-n-propylcarbonyl group, 1,2,2-trimethyl-n-propylcarbonyl group, 1-ethyl-l-methyl-n-propylcarbonyl group, 1-ethyl-2-methyl-n-propylcarbonyl group, cyclohexylcarbonyl group, 1-methyl-cyclopentylcarbonyl group, 2-methyl-cyclopentylcarbonyl group, 3-methyl-cyclopentylcarbonyl group, 1-ethyl-cyclobutylcarbonyl group, 2-ethyl-cyclobutylcarbonyl group, 3-ethyl-cyclobutylcarbonyl group, 1,2-dimethyl-cyclobutylcarbonyl group, 1,3-dimethyl-cyclobutylcarbonyl group, 2,2-dimethyl-cyclobutylcarbonyl group, 2,3-dimethyl-cyclobutylcarbonyl group, 2,4-dimethyl-cyclobutylcarbonyl group, 3,3-dimethyl-cyclobutylcarbonyl group, 1-n-propyl-cyclopropylcarbonyl group, 2-n-propyl-cyclopropylcarbonyl group, 1-i-propyl-cyclopropylcarbonyl group, 2-i-propyl-cyclopropylcarbonyl group, 1,2,2-trimethyl-cyclopropylcarbonyl group, 1,2,3-trimethyl-cyclopropylcarbonyl group, 2,2,3-trimethyl-cyclopropylcarbonyl group, 1-ethyl-2-methyl-cyclopropylcarbonyl group, 2-ethyl-l-methyl-cyclopropylcarbonyl group, 2-ethyl-2-methyl-cyclopropylcarbonyl group, and 2-ethyl-3-methyl-cyclopropylcarbonyl group.

Examples of the $C_{7-18}$ aralkyl group include groups resulting from the substitution of a hydrogen atom in the above-mentioned alkyl groups with an aryl group, including benzyl group, phenethyl group, 3-phenylpropyl group, 4-phenylbutyl group, 5-phenylpentyl group, 6-phenylhexyl group, α-naphthylmethyl group, β-naphthylmethyl group, 1-anthrylmethyl group, 2-anthrylmethyl group, 9-anthrylmethyl group, 1-phenanthrylmethyl group, 2-phenanthrylmethyl group, 3-phenanthrylmethyl group, 4-phenanthrylmethyl group, 9-phenanthrylmethyl group, α-naphthylethyl group, β-naphthylethyl group, 1-anthrylethyl group, 2-anthrylethyl group, 9-anthrylethyl group, 1-phenanthrylethyl group, 2-phenanthrylethyl group, 3-phenanthrylethyl group, 4-phenanthrylethyl group, and 9-phenanthrylethyl group.

From the viewpoint of allowing favorable gelation of the below-described various solvents using the gelator of the present invention, $R^1$ in formula [1] is preferably a linear or branched alkyl group having a carbon atom number of 12 to 20, a cyclic alkyl group having a carbon atom number of 12 to 20, or a linear or branched alkenyl group having a carbon atom number of 12 to 20, more preferably a linear alkyl group having a carbon atom number of 14 to 20, and most preferably n-octadecyl group.

In formula [1], Ar is preferably a phenyl group unsubstituted or optionally substituted with at least one substituent selected from the group consisting of a $C_{1-10}$ alkyl group, a halogen atom, and a $C_{7-18}$ aralkyl group. More preferably, Ar is a phenyl group unsubstituted or optionally substituted with at least one substituent selected from the group consisting of a $C_{1-5}$ alkyl group, a halogen atom, and a $C_{7-10}$ aralkyl group; from the viewpoint of exhibiting a more favorable gelation ability, Ar is particularly preferably an unsubstituted phenyl group or a phenyl group substituted with a tert-butyl group, a benzyl group, or a bromo group.

It is believed that when the compound of formula [1] as the gelator of the present invention is added to the below-described various solvents, it self-assembles to form fibrous or lamellar secondary assemblies, which contribute to the gelation of the solvents. Thus, suitable or optimal groups may be selected as $R^1$ and Ar in formula [1], in consideration of the degree of affinity of the secondary assemblies for the solvent for gelation, or the degree of solubility of the compound of formula [1] in the solvent for gelation.

The compound of formula [1] is also contemplated by the present invention.

In particular, in preferred compounds, $R^1$ in formula [1] is preferably a linear or branched alkyl group having a carbon atom number of 12 to 20, a cyclic alkyl group having a carbon atom number of 12 to 20, or a linear or branched alkenyl group having a carbon atom number of 12 to 20, more preferably a linear alkyl group having a carbon atom number of 14 to 20, and most preferably n-octadecyl group.

Moreover, in preferred compounds, Ar in formula [1] is preferably a phenyl group unsubstituted or substituted with at least one substituent selected from the group consisting of a $C_{1-10}$ alkyl group, a $C_{6-18}$ aryloxy group, a chloro group, a bromo group, a nitro group, a $C_{2-10}$ alkylcarbonyl group, and a $C_{7-18}$ aralkyl group.

In particular, Ar is preferably a phenyl group unsubstituted or substituted with at least one substituent selected from the group consisting of a $C_{1-5}$ alkyl group, a chloro group, a bromo group, a nitro group, a $C_{2-10}$ alkylcarbonyl group, and a $C_{7-10}$ aralkyl group.

In particularly preferred compounds, Ar is preferably an unsubstituted phenyl group or a phenyl group substituted with a tert-butyl group, a 3,5-di-t-butyl group, an o-isopropyl group, a m-isopropyl group, a 3,5-dimethyl group, a phenoxy group, a p-chloro group, a p-bromo group, an o-bromo group, a p-nitro group, a n-pentylcarbonyl group, or a benzyl group, more preferably a phenyl group substituted with a benzyl group, and most preferably a phenyl group substituted with an o-benzyl group.

The compound of formula [1] can be easily obtained by reacting, for example, a long-chain alkyl or long-chain alkenyl ester compound of isocyanic acid ($R^1$—NCO, wherein $R^1$ is as defined above in formula [1]) and an aryl compound having an amino group (Ar—$NH_2$, wherein Ar is as defined above in formula [1]) in an organic solvent.

While usable organic solvents in this reaction are not particularly limited so long as they dissolve the ester compound and the aryl compound, examples thereof include alcohols (for example, ethanol, propanol, butanol, and octanol), cellosolves (for example, methoxyethanol and ethoxyethanol), aprotic polar organic solvents (for example, N,N-dimethylformamide (DMF), dimethylsulfoxide (DMSO), N,N-dimethylacetamide, tetramethylurea, sulfolane, N-methylpyrrolidone, and N,N-dimethylimidazolidinone), ethers (for example, diethyl ether, diisopropyl ether, t-butyl methyl ether (TBME), tetrahydrofuran, and dioxane), aliphatic hydrocarbons (for example, pentane, hexane, cyclohexane, octane, decane, decalin, and petroleum ether), aromatic hydrocarbons (such as benzene, chlorobenzene, o-dichlorobenzene, nitrobenzene, toluene, xylene, mesitylene, and tetralin), halogenated hydrocarbons (for example, chloroform, dichloromethane, dichloroethane, and carbon tetrachloride), ketones (such as acetone, methyl ethyl ketone, methyl butyl ketone, and methyl isobutyl ketone), lower fatty acid esters (for example, methyl acetate, ethyl acetate, butyl acetate, and methyl propionate), alkoxy alkanes (for example, dimethoxyethane and diethoxyethane), and nitriles (for example, acetonitrile, propionitrile, and butyronitrile).

The reaction temperature may be selected, as appropriate, from room temperature (around 25° C.) to not higher than the reflux temperature of the organic solvent to be used in the reaction, and the reaction time may be selected, as appropriate, from about 1 hour to about 5 days.

After the completion of the reaction, the solvent is distilled off, and the resulting product may be purified, as required, using known purification methods such as various chromatography methods, a recrystallization method, a reprecipitation method, a distillation method, washing, and the like.

[Gel]

A gel of the present invention can be obtained by gelation of a solvent with the above-described gelator. Specific examples of methods for producing the gel of the present invention include a method in which a predetermined amount of the gelator is dissolved by heating in a solvent, and then the solution is cooled. Typically, when the gelator is dissolved by heating, it is preferably completely dissolved.

As used herein, "gelation" refers to a state in which a flowable liquid has lost its flowability.

For gelation of the solvent, the amount of the gelator of the present invention to be used is typically 0.001 to 20% by mass, for example, 0.05 to 5% by mass, based on the mass of the solvent for gelation, and is typically 0.001 to 20 w/v %, for example, 0.05 to 5 w/v %, based on the volume of the solvent for gelation, although not particularly limited thereto so long as the effects of the present invention are achieved.

While the solvent is not particularly limited so long as it does not prevent gelation, preferred specific examples thereof include hydrophobic organic solvents, hydrophilic organic solvents, mixed solvents of water and hydrophilic organic solvents (herein referred to as hydrophilic organic solutions), and ionic liquids.

The gel of the present invention is formed by including the above-described gelator, and a hydrophobic organic solvent, a hydrophilic organic solvent, a hydrophilic organic solution, or an ionic liquid.

Preferred specific examples of the hydrophobic organic solvent include vegetable oils such as olive oil, coconut oil, castor oil, jojoba oil, and sunflower oil; esters such as cetyl octanoate, isopropyl myristate, and isopropyl palmitate; and hydrocarbons such as toluene, xylene, n-hexane, cyclohexane, octane, squalane, liquid paraffin (mineral oil), silicone oils, and hydrogenated polyisobutene.

Among the above, preferred as the hydrophobic organic solvent are olive oil, isopropyl myristate, toluene, cyclohexane, squalane, liquid paraffin, silicone oils such as linear silicones, cyclic silicones, alkyl-modified silicones, phenyl-modified silicones, dimethicone, and dimethiconol, and octane.

Products usable as the silicone oils include a linear silicone (trade name: 2-1184), cyclic silicones (decamethylcyclopentasiloxane (trade name: SH245) and the like), an alkyl-modified silicone (trade name: SS-3408), a phenyl-modified silicone (trade name: PH-1555), dimethicone (trade name: BY-11-0 series), dimethiconol (trade name: CB-1556), and the like available from Dow Corning Toray Co., Ltd., and decamethylcyclopentasiloxane (trade name: KF995) and the like available from Shin-Etsu Silicone Co., Ltd.

While the hydrophilic organic solvent and the hydrophilic organic solvent of the hydrophilic organic solution are not particularly limited, so long as they are organic solvents that dissolve in water at any proportions, examples thereof include an alcohol, acetone, cyclohexanone, acetonitrile, dioxane, glycerol, and dimethylsulfoxide.

The alcohol is preferably a water-soluble alcohol that freely dissolves in water, and more preferably a $C_{1-9}$ alcohol, a polyhydric alcohol, a higher alcohol, or a glyceride, for example. Specifically, examples of the $C_{1-9}$ alcohol include methanol, ethanol, 2-propanol, i-butanol, pentanol, hexanol, 1-octanol, and isooctanol; examples of the polyhydric alcohol include butanediol, ethylene glycol, propylene glycol, and polypropylene glycol; examples of the higher alcohol include octyldodecanol, stearyl alcohol, and oleyl alcohol; and examples of the glyceride include trioctanoin, caprylic/capric triglyceride, and glyceryl stearate.

Among the above, preferred as the hydrophilic organic solvent and the hydrophilic organic solvent to be used in the hydrophilic organic solution are methanol, ethanol, 2-propanol, i-butanol, pentanol, hexanol, 1-octanol, isooctanol, acetone, cyclohexanone, acetonitrile, dioxane, glycerol, butanediol, propylene glycol, ethylene glycol, and dimethylsulfoxide, and ethanol is more preferred.

While the proportion of the hydrophilic organic solvent in the hydrophilic organic solution to be used herein is not particularly limited, it may be, for example, 10 to 90 wt %.

As the ionic liquid, those generally known as "ionic liquids" can be used, including, for example, a combination of a cationic species selected from the group consisting of imidazolium, pyridinium, piperidinium, pyrrolidinium, phosphonium, ammonium, and sulfonium, and an anionic species selected from the group consisting of a halogen, a carboxylate, a sulfate, a sulfonate, a thiocyanate, a nitrate, an aluminate, a borate, a phosphate, an amide, an antimonate, an imide, and a methide.

Examples of representative cationic species include 1,3-dialkylimidazolium ion, 1,2,3-trialkylimidazolium ion, N-alkylpyridinium ion, N-alkylpyrrolidinium ion, N-alkyl-N-alkoxyalkyl-pyrrolidinium ion, tetraalkylammonium ion, trialkyl-alkoxyalkyl-ammonium ion, tetraalkylphosphonium ion, and trialkylsulfonium ion.

Examples of representative anions include tetrafluoroborate ($BF_4^-$) ion, hexafluorophosphate ($PF_6^-$) ion, trifluoromethanesulfonate ($CF_3SO_3^-$) ion, hexafluoroantimonate ($SbF_6^-$) ion, bis(trifluoromethylsulfonyl)imide (($CF_3SO_2)_2N^-$) ion, bis(fluorosulfonyl)imide (($FSO_2)_2N^-$) ion, tris(trifluoromethylsulfonyl)methide (($CF_3SO_2)_3C^-$) ion, nitrate ($NO_3^-$) ion, trifluoromethylcarboxylate ($CF_3CO_2^-$) ion, carboxylate (acetate) ($CH_3CO_2^-$) ion, and chloroaluminate ($Al_2Cl_7^-$) ion.

A gel can be obtained by adding the gelator of the present invention to a medium such as the above-described hydrophobic organic solvent, hydrophilic organic solvent, hydrophilic organic solution, ionic liquid, or the like, dissolving the gelator by heating with stirring, as required, and then allowing the solution to stand at room temperature. The gel strength can be adjusted by adjusting the concentration of the gelator.

The gel formed with the gelator of the present invention may be mixed, as required, with various additives (organic compounds such as surfactants, ultraviolet absorbers, moisturizers, preservatives, antioxidants, perfumes, and physiologically active substances (medicinal components), and inorganic compounds such as titanium oxide, talc, mica, and water), in accordance with its use and the like, as long as it does not impair the gelation ability of the gelator.

The gelator of the present invention is capable of gelation of various solvents as described above, particularly gelation of hydrophobic organic solvents and ionic liquids. Thus, the gelator of the present invention and the gel obtained using the same can be used in materials for use in various fields, such as cosmetic or medical base materials, gel electrolytes, cell culture substrates, substrates for storage of biomolecules such as cells or proteins, base materials for external use, biochemical substrates, base materials for foods, contact lenses, diapers, artificial actuators, and base materials for dry-land farming. They can also be widely used as bioreactor carriers such as enzymes in research, medical, analytical, and various industries.

EXAMPLES

Examples are shown below to further clarify the features of the present invention, although the present invention is not limited to these examples.

The reagents used as synthesis materials in the following examples are shown below.

Octadecyl isocyanate was purchased from Tokyo Chemical Industry Co., Ltd.

Aniline, 2-naphthylamine, 2-nitroaniline, 3-nitroaniline, 4-nitroaniline, 3,5-dinitroaniline, 2-aminodiphenylmethane, 2-aminodiphenyl ether, 3-aminobiphenyl, 4-aminodiphenylmethane, 4-aminohexanophenone, 3-(tert-butyl)aniline, 4-(tert-butyl)aniline, 3,5-di-(tert-butyl)aniline, 2-chloroaniline, 3-chloroaniline, 4-chloroaniline, 2-bromoaniline, 3-bromoaniline, 4-bromoaniline, 2-isopropylaniline, 3-isopropylaniline, 4-isopropylaniline, and 3,5-dimethylaniline were purchased from Tokyo Chemical Industry Co., Ltd., Kanto Chemical Co., Inc., or Sigma Aldrich Co. LLC.

Acetonitrile, dichloromethane, 1,2-dichloroethane, and toluene were purchased from Tokyo Chemical Industry Co., Ltd. or Kanto Chemical Co., Inc.

Hexadeuterodimethyl sulfoxide (DMSO-$d_6$), hexadeuteroacetone (acetone-$d_6$), and 1,2,2,2-tetrachloroethane-d2 ($CDCl_2CDCl_2$) used for NMR measurements were purchased from Kanto Chemical Co., Inc. or Sigma Aldrich Co. LLC.

The solvents and the reagents used in the following gelation test and emulsion preparation are shown below.

Liquid paraffin, squalane, isopropyl myristate, and ethanol were purchased from Nacalai Tesque, Inc., Tokyo Chemical Industry Co., Ltd., or Matsuzaki-Kasei Co., Ltd., SH245 (decamethylcyclopentasiloxane) was purchased from Dow Corning Toray Co., Ltd., and ionic liquids were purchased from Tokyo Chemical Industry Co., Ltd. or Kanto Chemical Co., Inc.

Ethyl acetate, methylene chloride, chloroform, toluene, and n-hexane were purchased from Kanto Chemical Co., Inc., and dimethylsulfoxide (DMSO), acetonitrile, and 1,3-butanediol were purchased from Tokyo Chemical Industry Co., Ltd.

Pure water was used as water.

The apparatuses and conditions used in various measurements, analyses, and polymerization are shown below.

(1) $^1$H-NMR spectra

Apparatus: JNM ECA-600 from JEOL Ltd.

(2) Vortex mixer

Apparatus: VORTEX3 from IKA Ltd.

(3) Thin-layer chromatography (TLC)

TLC Silica gel 60 F254 from Merck Ltd.

Example 1: Synthesis of Gelators

<Synthesis of Monourea Compound of Formula 1>

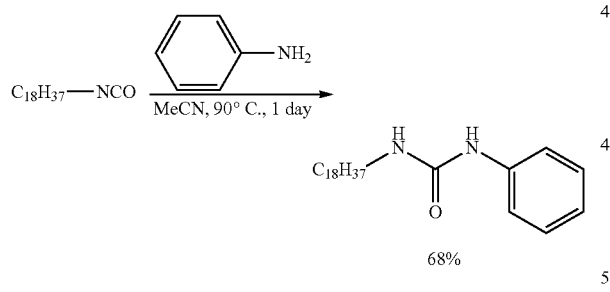

In an argon atmosphere, aniline (0.70 mL, 7.72 mmol) was dissolved in acetonitrile (100 mL), octadecyl isocyanate (2.65 mL, 7.72 mmol) was added thereto, and the mixture was stirred at 90° C. for 24 hours. After the completion of the reaction was confirmed by TLC, the solvent was concentrated, and the product precipitated as a solid was collected by filtration.

The product was purified by a recrystallization method with trichloromethane ($CHCl_3$) to obtain a monourea compound of formula 1 as a white solid (amount: 2.03 g, yield: 68%).

$^1$H NMR (400 MHz, DMSO-$d_6$) δ 0.85 (t, J=6.8 Hz, 3H), 1.23 (m, 30H), 1.40 (m, 2H), 3.04 (dt, J=5.6, 6.8 Hz, 2H), 6.17 (t, J=5.4 Hz, 1H), 6.86 (t, J=7.3 Hz, 1H), 7.19 (dd, J=7.3, 7.8 Hz, 2H), 7.36 (d, J=7.8 Hz, 2H), 8.44 (s, 1H).

<Synthesis of Monourea Compound of Formula 2>

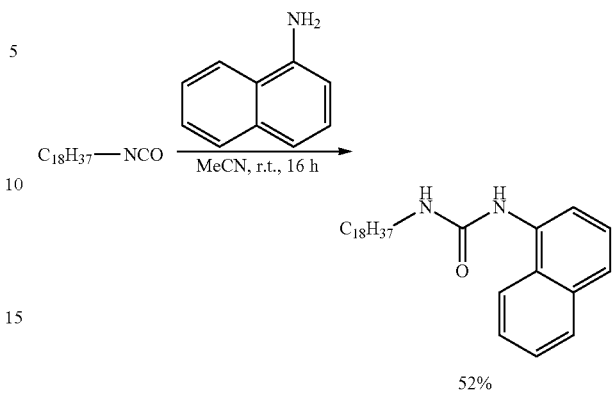

In an argon atmosphere, 2-naphthylamine (288 mg, 2.50 mmol) was dissolved in acetonitrile (100 mL), octadecyl isocyanate (0.85 mL, 2.50 mmol) was added thereto, and the mixture was stirred at room temperature (approximately 25° C.) for 16 hours. After the completion of the reaction was confirmed by TLC, the solvent was concentrated, and the product precipitated as a solid was collected by filtration.

The product was purified by a reprecipitation method with dichloromethane-hexane ($CH_2Cl_2$-hexane) to obtain a monourea compound of formula 2 as a white solid (amount: 571.3 mg, yield: 52%).

$^1$H NMR (600 MHz, DMSO-$d_6$) δ 0.85 (t, J=6.9 Hz, 3H), 1.23 (m, 30H), 1.46 (m, 2H), 3.14 (dt, J=5.6, 6.8 Hz, 2H), 6.61 (t, J=5.5 Hz, 1H), 7.40 (dd, J=7.6, 7.9 Hz, 1H), 7.49-7.54 (m, 3H), 7.88 (d, J=8.2 Hz, 1H), 7.99 (d, J=7.6 Hz, 1H), 8.07 (d, J=8.2 Hz, 1H), 8.50 (s, 1H).

<Synthesis of Monourea Compound of Formula 3>

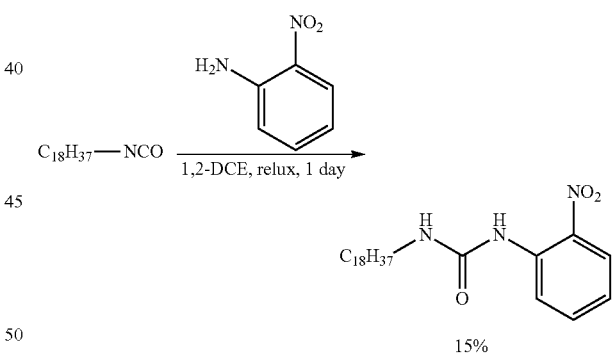

In an argon atmosphere, 2-nitroaniline (637 mg, 4.60 mmol) was dissolved in 1,2-dichloroethane (100 mL), octadecyl isocyanate (1.55 mL, 4.60 mmol) was added thereto, and the mixture was stirred under reflux for 24 hours. After the completion of the reaction was confirmed by TLC, the solvent was concentrated, and the product precipitated as a solid was collected by filtration.

The product was purified by washing the crude product with hexane to obtain a monourea compound of formula 3 as a yellow solid (amount: 300 mg, yield: 15%).

$^1$H NMR (400 MHz, DMSO-$d_6$) δ 0.85 (t, J=7.3 Hz, 3H), 1.23 (m, 30H), 1.41 (m, 2H), 3.08 (t, J=6.8 Hz, 2H), 7.12 (dd, J=8.3, 8.3 Hz, 1H), 7.51 (brs, 1H), 7.63 (dd, J=8.3, 8.3 Hz, 1H), 8.05 (d, J=8.3 Hz, 1H), 8.31 (d, J=8.3 Hz, 1H), 9.33 (s, 1H).

\<Synthesis of Monourea Compound of Formula 4\>

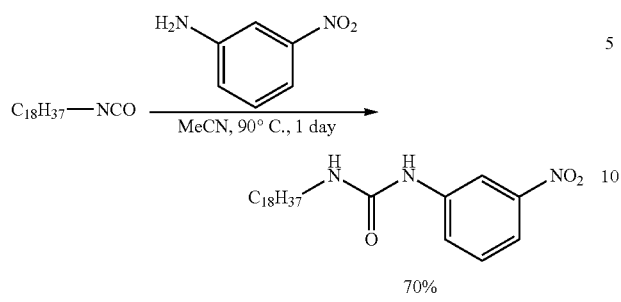

70%

In an argon atmosphere, 3-nitroaniline (282 mg, 2.04 mmol) was dissolved in acetonitrile (100 mL), octadecyl isocyanate (0.70 mL, 2.04 mmol) was added thereto, and the mixture was stirred at 90° C. for 24 hours. After the completion of the reaction was confirmed by TLC, the solvent was concentrated, and the product precipitated as a solid was collected by filtration.

The product was purified by a reprecipitation method with acetone-hexane to obtain a monourea compound of formula 4 as a white solid (amount: 620 mg, yield: 70%).

$^1$H NMR (400 MHz, acetone-d$_6$) δ 0.87 (t, J=6.8 Hz, 3H), 1.30 (m, 30H), 1.51 (m, 2H), 3.21 (t, J=6.8 Hz, 2H), 5.99 (brs, 1H), 7.48 (dd, J=8.3, 8.3 Hz, 1H), 7.73-7.77 (m, 2H), 8.40 (brs, 1H), 8.62 (dd, J=1.9, 2.2 Hz, 1H).

\<Synthesis of Monourea Compound of Formula 5\>

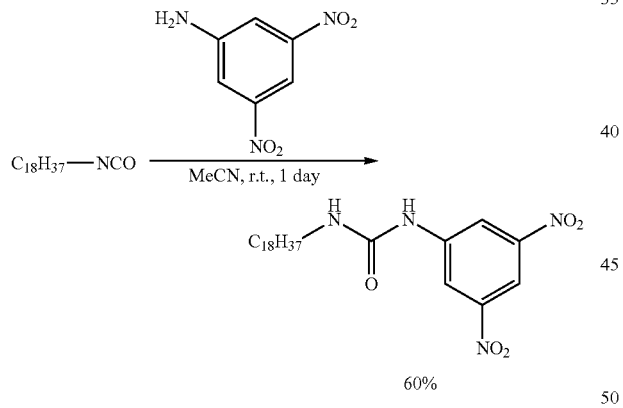

60%

In an argon atmosphere, 3,5-dinitroaniline (382 mg, 2.10 mmol) was dissolved in acetonitrile (100 mL), octadecyl isocyanate (0.71 mL, 2.06 mmol) was added thereto, and the mixture was stirred at room temperature (approximately 25° C.) for 24 hours. After the completion of the reaction was confirmed by TLC, the solvent was concentrated, and the product precipitated as a solid was collected by filtration.

The product was purified by washing the crude product with ethyl acetate to obtain a monourea compound of formula 6 as a yellow solid (amount: 602 mg, yield: 60%).

$^1$H NMR (400 MHz, DMSO-d$_6$) δ 0.84 (t, J=6.6 Hz, 3H), 1.22 (m, 30H), 1.43 (m, 2H), 3.09 (dt, J=5.6, 6.3 Hz, 2H), 6.67 (brs, 1H), 8.32 (s, 1H), 8.69 (s, 2H), 9.57 (brs, 1H).

\<Synthesis of Monourea Compound of Formula 6\>

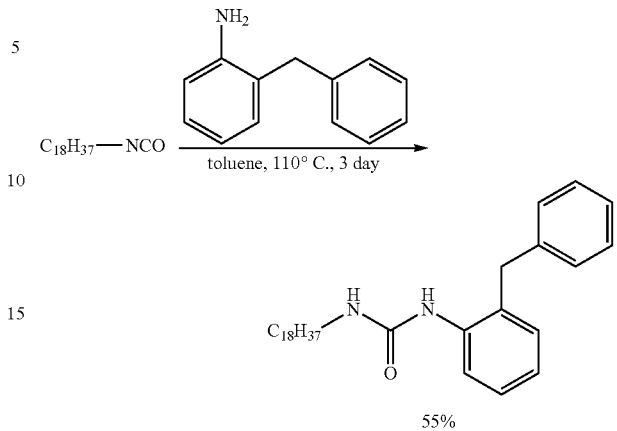

55%

In an argon atmosphere, 2-aminodiphenylmethane (500 mg, 1.80 mmol) was dissolved in toluene (100 mL), octadecyl isocyanate (0.62 mL, 1.80 mmol) was added thereto, and the mixture was stirred at 110° C. for 3 days. After the completion of the reaction was confirmed by TLC, the solvent was concentrated, and the product precipitated as a solid was collected by filtration.

The product was purified by washing with acetone to obtain a monourea compound of formula 7 as a white solid (amount: 498 mg, yield: 55%).

$^1$H NMR (600 MHz, DMSO-d$_6$) δ 0.85 (t, J=6.9 Hz, 3H), 1.23 (m, 30H), 1.40 (m, 2H), 3.05 (dt, J=5.6, 6.9 Hz, 2H), 3.91 (s, 2H), 6.42 (t, J=5.5 Hz 1H), 6.90 (dd, J=7.6, 7.6 Hz, 1H), 6.99 (d, J=6.9 Hz, 1H), 7.11 (dd, J=6.9, 6.9 Hz, 1H), 7.15-7.18 (m, 3H), 7.27 (dd, J=7.6, 7.6 Hz, 2H), 7.69 (s, 1H), 7.73 (d, J=7.6 Hz, 1H).

\<Synthesis of Monourea Compound of Formula 7\>

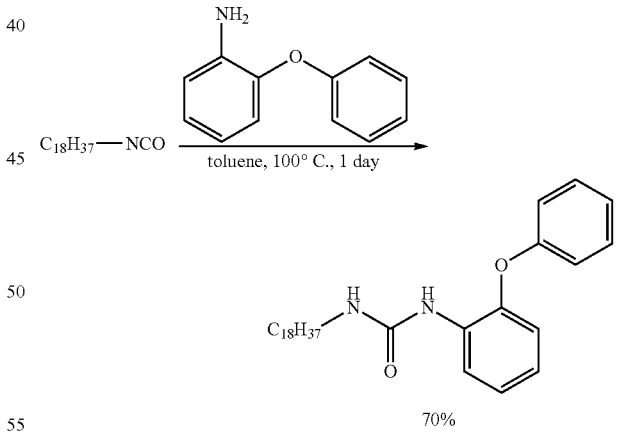

70%

In an argon atmosphere, 2-aminodiphenylether (348 mg, 2.04 mmol) was dissolved in toluene (100 mL), octadecyl isocyanate (0.70 mL, 2.04 mmol) was added thereto, and the mixture was stirred at 100° C. for 1 day. After the completion of the reaction was confirmed by TLC, the solvent was concentrated, and the product precipitated as a solid was collected by filtration.

The product was purified by a reprecipitation method with dichloromethane-hexane (CH$_2$Cl$_2$-hexane) to obtain a monourea compound of formula 8 as a white solid (amount: 620 mg, yield: 70%).

$^1$H NMR (600 MHz, acetone-d$_6$) δ 0.88 (t, J=6.9 Hz, 3H), 1.28 (m, 30H), 1.48 (m, 2H), 3.19 (dt, J=5.5, 6.9 Hz, 2H), 6.22 (brs, 1H), 6.80 (d, J=8.2 Hz, 1H), 6.88 (dd, J=8.2, 8.2 Hz, 1H), 6.95 (d, J=7.6 Hz, 2H), 7.07 (dd, J=6.9, 8.2 Hz, 1H), 7.12 (dd, J=6.8, 7.6, 1H), 7.37 (dd, J=7.6, 8.3 Hz, 2H), 7.70 (s, 1H), 8.43 (d, J=8.3 Hz, 1H).

<Synthesis of Monourea Compound of Formula 8>

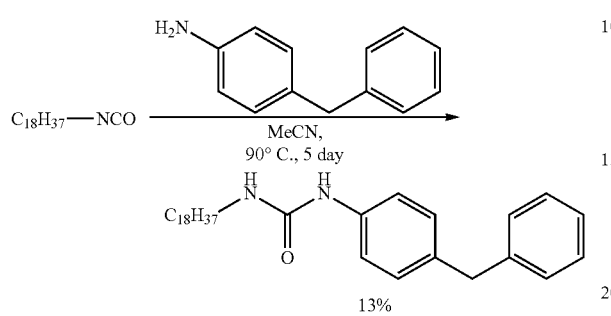

13%

In an argon atmosphere, 4-aminodiphenylmethane (416 mg, 2.27 mmol) was dissolved in acetonitrile (100 mL), octadecyl isocyanate (0.9 mL, 2.27 mmol) was added thereto, and the mixture was stirred at 90° C. for 5 days. After the completion of the reaction was confirmed by TLC, the solvent was concentrated, and the product precipitated as a solid was collected by filtration.

The product was purified by a reprecipitation method with acetone-hexane to obtain a monourea compound of formula 10 as a white solid (amount: 171.5 mg, yield: 13%).

$^1$H NMR (600 MHz, DMSO-d$_6$) δ 0.85 (t, J=6.9 Hz, 3H), 1.23 (m, 30H), 1.39 (m, 2H), 3.03 (dt, J=6.2, 6.5 Hz, 2H), 3.38 (s, 2H), 6.07 (brs, 1H), 7.05 (d, J=8.9 Hz, 2H), 7.16-7.19 (m, 3H), 7.26 (d, J=8.2 Hz, 2H), 7.27 (d, J=8.3 Hz, 2H), 8.31 (s, 1H).

<Synthesis of Monourea Compound of Formula 9>

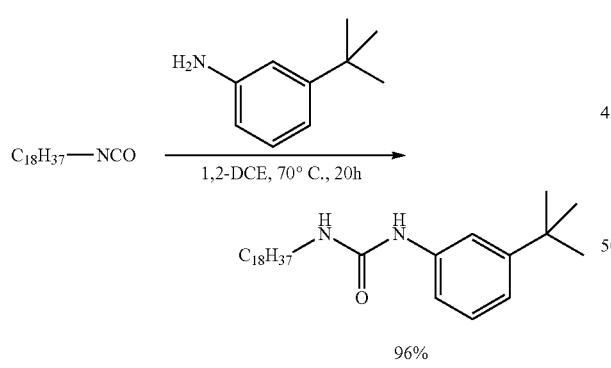

96%

In an argon atmosphere, 3-(tert-butyl)aniline (290 mg, 1.94 mmol) was dissolved in 1,2-dichloroethane (100 mL), octadecyl isocyanate (0.66 mL, 1.94 mmol) was added thereto, and the mixture was stirred at 70° C. for 20 hours. After the completion of the reaction was confirmed by TLC, the solvent was concentrated, and the product precipitated as a solid was collected by filtration.

The product was purified by a reprecipitation method with dichloromethane-hexane (CH$_2$Cl$_2$-hexane) to obtain a monourea compound of formula 12 as a white solid (amount: 830 mg, yield: 96%).

$^1$H NMR (600 MHz, DMSO-d$_6$) δ 0.86 (t, J=6.9 Hz, 3H), 1.26 (m, 39H), 1.43 (m, 2H), 3.07 (dt, J=5.5, 6.9 Hz, 2H), 5.98 (t, J=5.6 Hz, 1H), 6.91 (d, J=7.6 Hz, 1H), 7.12 (dd, J=7.6, 8.2 Hz, 1H), 7.21 (d, J=8.2 Hz, 1H), 7.38 (s, 1H), 8.22 (s, 1H).

<Synthesis of Monourea Compound of Formula 10>

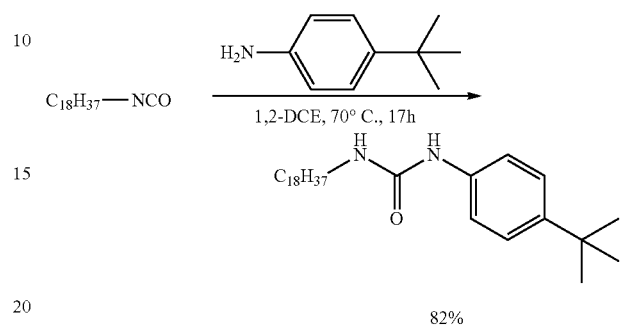

82%

In an argon atmosphere, 4-(tert-butyl)aniline (382 mg, 2.56 mmol) was dissolved in 1,2-dichloroethane (100 mL), octadecyl isocyanate (0.87 mL, 2.56 mmol) was added thereto, and the mixture was stirred at 70° C. for 17 hours. After the completion of the reaction was confirmed by TLC, the solvent was concentrated, and the product precipitated as a solid was collected by filtration.

The product was purified by a reprecipitation method with dichloromethane-hexane (CH$_2$Cl$_2$-hexane) to obtain a monourea compound of formula 13 as a white solid (amount: 934 mg, yield: 82%).

$^1$H NMR (400 MHz, DMSO-d$_6$) δ 0.85 (t, J=6.8 Hz, 3H), 1.23 (M, 39H), 1.40 (m, 2H), 3.04 (dt, J=5.9, 6.8 Hz, 2H), 6.02 (t, J=5.9 Hz, 1H), 7.21 (d, J=8.8 Hz, 2H), 7.27 (d, J=8.8 Hz, 2H), 8.25 (s, 1H).

<Synthesis of Monourea Compound of Formula 11>

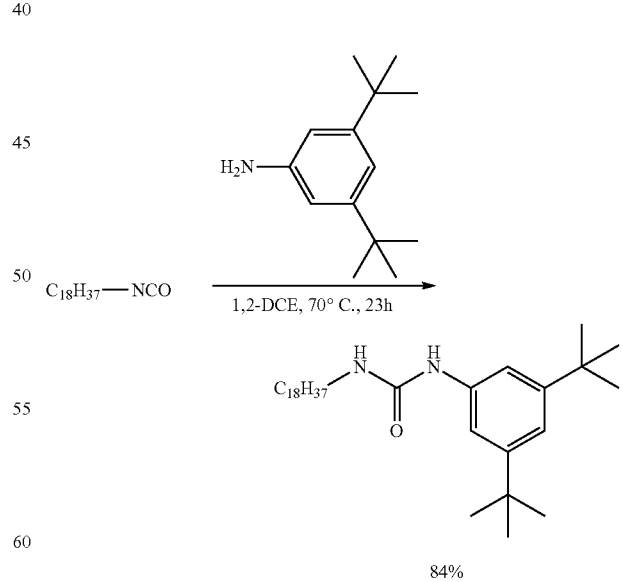

84%

In an argon atmosphere, 3,5-di-(tert-butyl)aniline (287 mg, 1.40 mmol) was dissolved in 1,2-dichloroethane (100 mL), octadecyl isocyanate (0.48 mL, 1.40 mmol) was added thereto, and the mixture was stirred at 70° C. for 23 hours.

After the completion of the reaction was confirmed by TLC, the solvent was concentrated, and the product precipitated as a solid was collected by filtration.

The product was purified by a reprecipitation method with dichloromethane-hexane ($CH_2Cl_2$-hexane) to obtain a monourea compound of formula 14 as a white solid (amount: 590 mg, yield: 84%).

$^1$H NMR (400 MHz, DMSO-$d_6$) δ 0.86 (t, J=6.9 Hz, 3H), 1.25 (m, 48H), 1.42 (m, 2H), 3.07 (dt, J=5.7, 6.9 Hz, 2H), 5.93 (t, J=5.6 Hz, 1H), 6.94 (s, 1H), 7.23 (s, 2H), 8.18 (s, 1H).

<Synthesis of Monourea Compound of Formula 12>

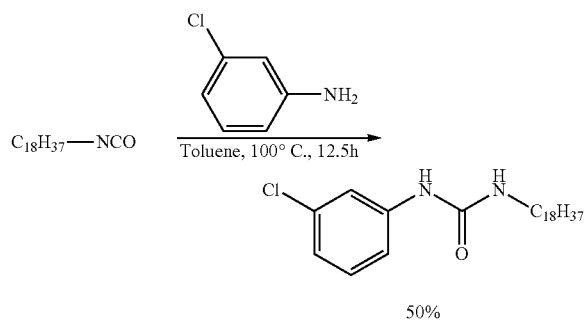

50%

In an argon atmosphere, 3-chloroaniline (1.23 mL, 12.0 mmol) was dissolved in toluene (100 mL), octadecyl isocyanate (4.12 mL, 12.0 mmol) was added thereto, and the mixture was stirred at 100° C. for 12.5 hours. After the completion of the reaction was confirmed by TLC, the solvent was concentrated, and the product precipitated as a solid was collected by filtration.

The product was purified by a recrystallization method with ethyl acetate to obtain a monourea compound of formula 16 as a white solid (amount: 2.50 g, yield: 50%).

$^1$H NMR (600 MHz, DMSO-$d_6$) δ 0.85 (t, J=6.9 Hz, 3H), 1.23 (m, 30H), 1.40 (m, 2H), 3.05 (dt, J=5.5, 6.9 Hz, 2H), 6.26 (t, J=5.2 Hz, 1H), 6.91 (d, J=8.3 Hz, 1H), 7.15 (d, J=8.3 Hz, 1H), 7.21 (dd, J=8.3, 8.3 Hz, 1H), 7.66 (s, 1H), 8.68 (s, 1H).

<Synthesis of Monourea Compound of Formula 13>

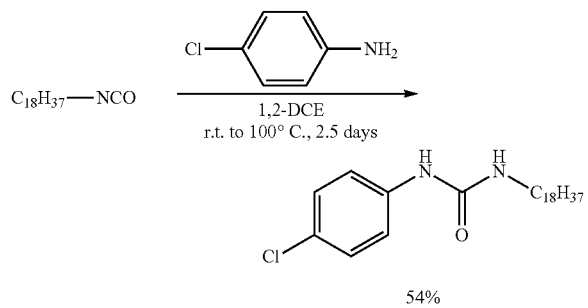

54%

In an argon atmosphere, 4-chloroaniline (666.5 mg, 5.22 mmol) was dissolved in 1,2-dichloroethane (100 mL), octadecyl isocyanate (2.00 mL, 5.70 mmol) was added thereto, and the mixture was stirred at room temperature (approximately 25° C.) to 100° C. for 2.5 days. After the completion of the reaction was confirmed by TLC, the solvent was concentrated, and the product precipitated as a solid was collected by filtration.

The product was purified by a recrystallization method with ethyl acetate-hexane to obtain a monourea compound of formula 17 as a white solid (amount: 1.21 g, yield: 54%).

$^1$H NMR (600 MHz, acetone-$d_6$) δ 0.87 (t, J=6.8 Hz, 3H), 1.28 (m, 30H), 1.50 (m, 2H), 3.19 (t, J=6.8 Hz, 2H), 5.81 (brs, 1H), 7.21 (d, J=8.9 Hz, 2H), 7.51 (d, J=8.9 Hz, 2H), 8.00 (s, 1H).

<Synthesis of Monourea Compound of Formula 14>

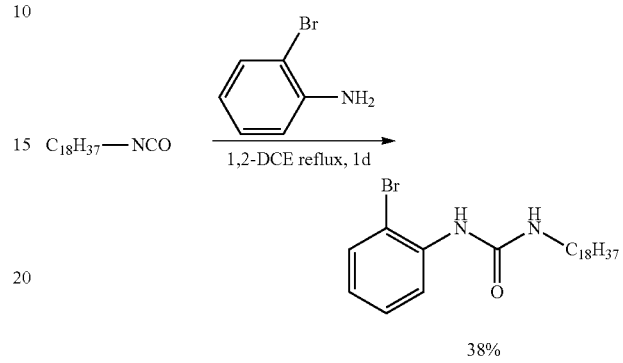

38%

In an argon atmosphere, 2-bromoaniline (1.10 g, 6.40 mmol) was dissolved in 1,2-dichloroethane (100 mL), octadecyl isocyanate (2.15 mL, 6.40 mmol) was added thereto, and the mixture was stirred under reflux for 1 day. After the completion of the reaction was confirmed by TLC, the solvent was concentrated, and the product precipitated as a solid was collected by filtration.

The product was purified by a recrystallization method with trichloromethane ($CHCl_3$) to obtain a monourea compound of formula 18 as a white solid (amount: 1.14 g, yield: 38%).

$^1$H NMR (600 MHz, $CDCl_2CDCl_2$) δ 0.88 (t, J=6.8 Hz, 3H), 1.28 (m, 30H), 1.54 (m, 2H), 3.24 (t, J=7.6 Hz, 2H), 4.73 (brs, 1H), 6.66 (brs, 1H), 6.94 (dd, J=8.2, 8.2 Hz, 1H), 7.30 (dd, J=8.2, 8.2 Hz, 1H), 7.54 (d, J=8.2 Hz, 1H), 8.05 (d, J=8.2 Hz, 1H).

<Synthesis of Monourea Compound of Formula 15>

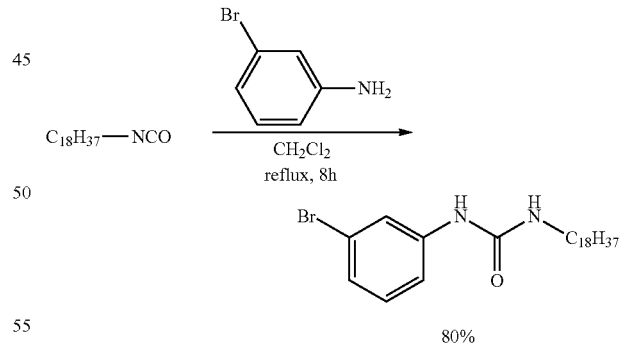

80%

In an argon atmosphere, 3-bromoaniline (0.48 mL, 4.42 mmol) was dissolved in dichloromethane (100 mL), octadecyl isocyanate (1.53 mL, 4.47 mmol) was added thereto, and the mixture was stirred under reflux for 8 hours. After the completion of the reaction was confirmed by TLC, the solvent was concentrated, and the product precipitated as a solid was collected by filtration.

The product was purified by a recrystallization method with ethanol to obtain a monourea compound of formula 19 as a white solid (amount: 1.67 g, yield: 80%).

$^1$H NMR (600 MHz, DMSO-d$_6$) δ 0.85 (t, J=6.8 Hz, 3H), 1.23 (m, 30H), 1.40 (m, 2H), 3.05 (dt, J=5.5, 6.8 Hz, 2H), 6.25 (brs, 1H), 7.04 (d, J=6.9 Hz, 1H), 7.15 (dd, J=7.0, 8.8 Hz, 1H), 7.19 (d, J=8.9 Hz, 1H), 7.81 (s, 1H), 8.66 (s, 1H).

<Synthesis of Monourea Compound of Formula 16>

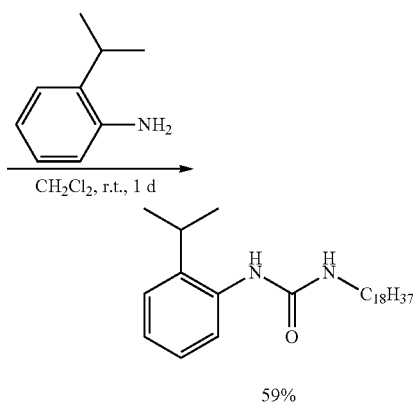

59%

In an argon atmosphere, 2-isopropylaniline (1.45 g, 10.8 mmol) was dissolved in dichloromethane (100 mL), octadecyl isocyanate (1.53 mL, 4.47 mmol) was added thereto, and the mixture was stirred at room temperature (approximately 25° C.) for 1 day. After the completion of the reaction was confirmed by TLC, the solvent was concentrated, and the product precipitated as a solid was collected by filtration.

The product was purified by reprecipitating the crude product with trichloromethane-hexane (CHCl$_3$-hexane), followed by washing the crude product with methanol-acetone, to obtain a monourea compound of formula 21 as a white solid (amount: 2.74 g, yield: 59%).

$^1$H NMR (600 MHz, CDCl$_2$CDCl$_2$) δ 0.85 (t, J=6.8 Hz, 3H), 1.21 (m, 36H), 1.41 (m, 2H), 3.14 (m, 3H), 4.48 (brs, 1H), 6.19 (brs, 1H), 7.21 (dd, J=7.6, 7.6 Hz, 1H), 7.26 (m, 2H), 7.33 (d, J=7.6 Hz, 1H).

<Synthesis of Monourea Compound of Formula 17>

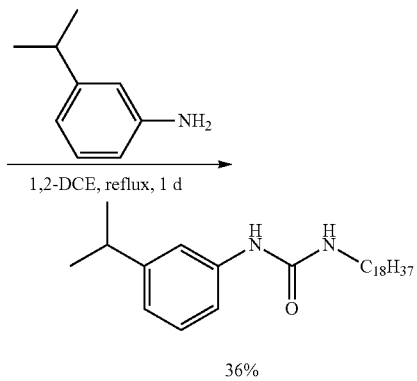

36%

In an argon atmosphere, 3-isopropylaniline (941 mg, 7.0 mmol) was dissolved in 1,2-dichloroethane (100 mL), octadecyl isocyanate (2.35 mL, 6.34 mmol) was added thereto, and the mixture was stirred under reflux for 1 day. After the completion of the reaction was confirmed by TLC, the solvent was concentrated, and the product precipitated as a solid was collected by filtration.

The product was purified by a recrystallization method with trichloromethane (CHCl$_3$) to obtain a monourea compound of formula 22 as a white solid (amount: 1.08 g, yield: 36%).

$^1$H NMR (600 MHz, CDCl$_2$CDCl$_2$) δ 0.88 (t, J=6.9 Hz, 3H), 1.25 (m, 36H), 1.50 (m, 2H), 2.88 (sep, J=6.9 Hz, 1H), 3.21 (t, J=7.6 Hz, 2H), 4.58 (brs, 1H), 6.34 (brs, 1H), 7.00 (d, J=8.2 Hz, 1H), 7.11-7.12 (m, 2H), 7.26 (dd, J=8.3, 8.3 Hz, 1H).

<Synthesis of Monourea Compound of Formula 18>

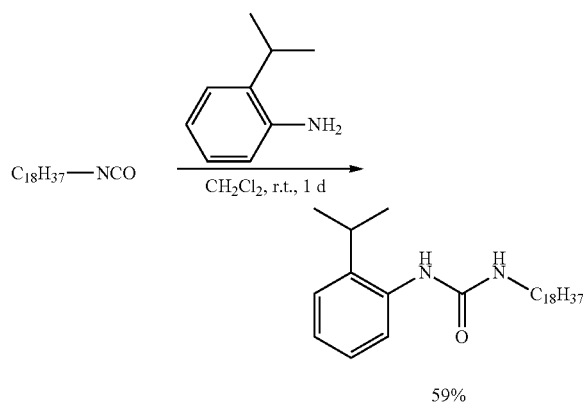

71%

In an argon atmosphere, 3,5-dimethylaniline (1.16 g, 9.61 mmol) was dissolved in dichloromethane (100 mL), octadecyl isocyanate (3.80 mL, 10.9 mmol) was added thereto, and the mixture was stirred at room temperature (approximately 25° C.) for 1 day. After the completion of the reaction was confirmed by TLC, the solvent was concentrated, and the product precipitated as a solid was collected by filtration.

The product was purified by reprecipitating the crude product with ethyl acetate-hexane, followed by washing the crude product with methanol-trichloroethane (CHCl$_3$), to obtain a monourea compound of formula 24 as a white solid (amount: 2.85 g, yield: 71%).

$^1$H NMR (400 MHz, CDCl$_3$) δ 0.88 (t, J=6.8 Hz, 3H), 1.25 (m, 30H), 1.50 (m, 2H), 2.28 (s, 6H), 3.23 (t, J=7.3 Hz, 2H), 4.51 (brs, 1H), 6.19 (brs, 1H), 6.75 (s, 1H), 6.88 (s, 2H).

<Synthesis of Monourea Compound of Formula 19>

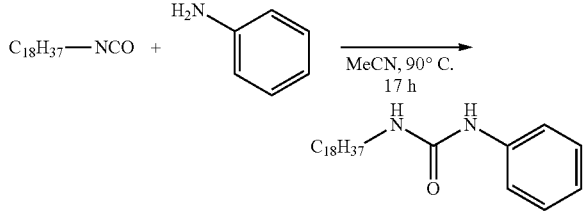

An apparatus (a reaction flask, a three-way stopcock, a rotor, a septum, and a Dimroth condenser) was set up, the inside of the apparatus was dried with a heat gun, and then the apparatus was purged with argon. Acetonitrile, aniline (0.7 mL, 8.03 mmol), and octyl isocyanate (1.4 mL, 8.03 mmol) were placed in this order in the reaction flask, and the mixture was stirred at 90° C. for 17 hours. After the completion of the reaction was confirmed by TLC, the precipitated solid was collected by filtration, and washed with acetonitrile to obtain a target product as a white solid (yield: 87%, 1.73 g).

$^1$H-NMR (CDCl$_3$) δ: 7.33 (2H, t, J=7.9 Hz), 7.29 (2H, d, J=7.6 Hz), 7.12 (1H, t, J=7.6 Hz), 6.25 (1H, s), 4.71 (1H, s), 3.25 (2H, t, J=6.9 Hz), 1.54-1.49 (2H, m), 1.30 (10H, m), 0.89 (3H, t, J=7.2 Hz).

<Synthesis of Monourea Compound of Formula 20>

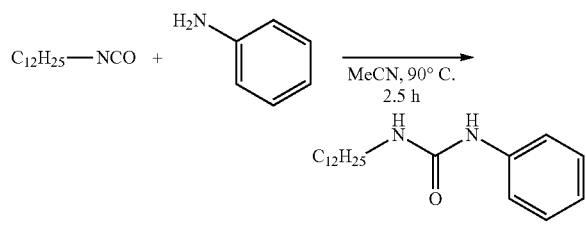

An apparatus (a reaction flask, a three-way stopcock, a rotor, a septum, and a Dimroth condenser) was set up, the inside of the apparatus was dried with a heat gun, and then the apparatus was purged with argon. Acetonitrile, aniline (0.6 mL, 6.57 mmol), and dodecyl isocyanate (1.6 mL, 6.57 mmol) were placed in this order in the reaction flask, and the mixture was stirred at 90° C. for 2.5 hours. After the completion of the reaction was confirmed by TLC, the precipitated solid was collected by filtration, and washed with acetonitrile to obtain a target product as a white solid (yield: 95%, 1.90 g).

$^1$H-NMR (600 MHz, CDCl$_3$) δ=7.32 (2H, t, J=7.9 Hz), 7.28 (2H, d, J=7.6 Hz), 7.11 (1H, t, J=7.6 Hz), 6.15 (1H, s), 4.64 (1H, s), 3.24 (2H, t, J=6.9 Hz), 1.50-1.27 (20H, m), 0.88 (3H, t, J=6.9 Hz).

<Synthesis of Monourea Compound of Formula 21>

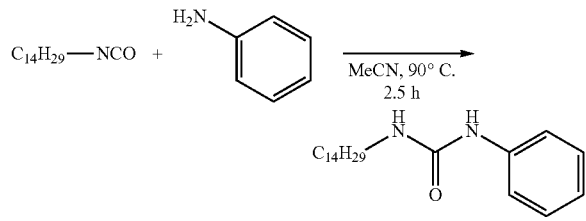

An apparatus (a reaction flask, a three-way stopcock, a rotor, and a septum) was set up, the inside of the apparatus was dried with a heat gun, and then the apparatus was purged with argon. Acetonitrile, aniline (0.6 mL, 6.01 mmol), and tetradecyl isocyanate (1.7 mL, 6.01 mmol) were placed in this order in the reaction flask, and the mixture was stirred at 90° C. for 2.5 hours. After the completion of the reaction was confirmed by TLC, the resulting solid was collected by filtration, and thermally recrystallized from chloroform to obtain a target product as a white solid (yield: 79%, 1.57 g).

$^1$H-NMR (600 MHz, CDCl$_3$) δ=7.33 (2H, t, J=7.9 Hz), 7.27 (2H, d, J=7.6 Hz), 7.11 (1H, t, J=7.6 Hz), 6.11 (1H, s), 4.61 (1H, s), 3.24 (2H, d, J=6.9 Hz), 1.50-1.27 (24H, m), 0.88 (3H, t, J=7.2 Hz).

<Synthesis of Monourea Compound of Formula 22>

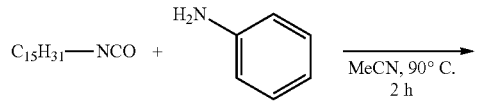

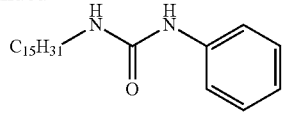

An apparatus (a Schlenk tube, a rotor, and a septum) was set up, the inside of the apparatus was dried with a heat gun, and then the apparatus was purged with argon.

Acetonitrile, aniline (0.1 mL, 1.02 mmol), and pentadecyl isocyanate (0.3 mL, 1.02 mmol) were placed in this order in the Schlenk tube, and the mixture was stirred at 90° C. for 2 hours. After the completion of the reaction was confirmed by TLC, the resulting solid was collected by filtration, and thermally recrystallized from trichloromethane (CHCl$_3$) to obtain a target product as a white solid (yield: 39%, 139.3 mg).

$^1$H-NMR (600 MHz, DMSO-d$_6$) δ=8.42 (1H, s), 7.36 (2H, d, J=7.6 Hz), 7.19 (2H, dd, J=7.6, 7.6 Hz), 6.86 (1H, t, J=7.2 Hz), 6.15 (1H, s), 3.05 (2H, t, J=6.4 Hz), 1.40-1.25 (26H, m), 0.85 (3H, t, J=6.9 Hz).

<Synthesis of Monourea Compound of Formula 23>

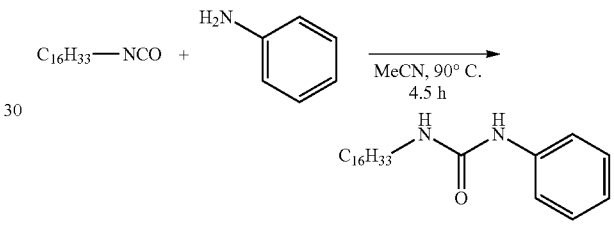

An apparatus (a reaction flask, a three-way stopcock, a rotor, a septum, and a Dimroth condenser) was set up, the inside of the apparatus was dried with a heat gun, and then the apparatus was purged with argon. Acetonitrile, aniline (0.5 mL, 5.55 mmol), and hexadecyl isocyanate (1.7 mL, 5.55 mmol) were placed in this order in the reaction flask, and the mixture was stirred at 90° C. for 4.5 hours. After the completion of the reaction was confirmed by TLC, the precipitated solid was collected by filtration, and thermally recrystallized from chloroform to obtain a target product as a white solid (yield: 73%, 1.46 g).

$^1$H-NMR (600 MHz, CDCl$_3$) δ=7.33 (2H, t, J=7.9 Hz), 7.27 (2H, d, J=7.6 Hz), 7.11 (1H, t, J=7.2 Hz), 6.13 (1H, s), 4.63 (1H, s), 3.24 (2H, t, J=6.9 Hz), 1.50-1.29 (28H, m), 0.88 (3H, t, J=7.2 Hz).

<Synthesis of Monourea Compound of Formula 24>

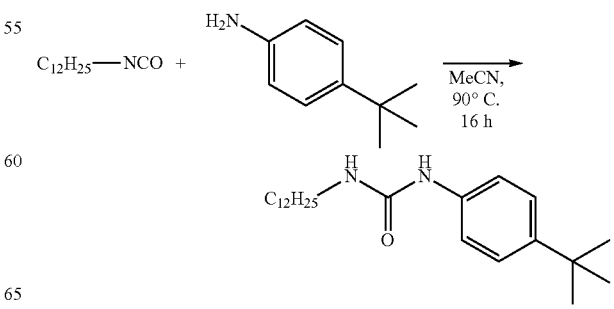

An apparatus (a reaction flask, a three-way stopcock, a rotor, a septum, and a Dimroth condenser) was set up, the inside of the apparatus was dried with a heat gun, and then the apparatus was purged with argon. Acetonitrile, 4-t-butylaniline (0.9 mL, 5.55 mmol), and dodecyl isocyanate (1.4 mL, 5.55 mmol) were placed in this order in the reaction flask, and the mixture was stirred at 90° C. for 16 hours. After the completion of the reaction was confirmed by TLC, the precipitated solid was collected by filtration, and washed with acetonitrile to obtain a target product as a white solid (yield: 96%, 1.92 g).

$^1$H-NMR (600 MHz, CDCl$_3$) δ=7.35 (2H, d, J=8.9 Hz), 7.17 (2H, d, J=8.9 Hz), 6.04 (1H, s), 4.64 (1H, s), 3.23 (2H, t, J=6.2 Hz), 1.49-1.27 (29H, m), 0.88 (3H, t, J=6.9 Hz).

<Synthesis of Monourea Compound of Formula 25>

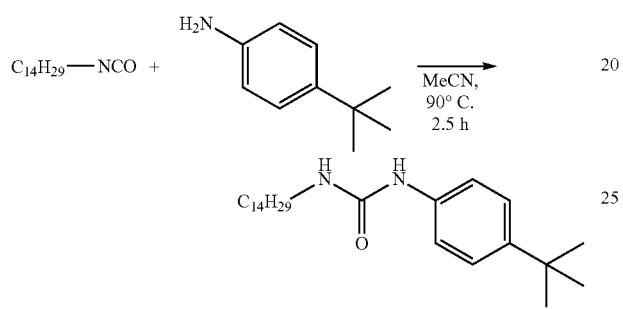

An apparatus (a reaction flask, a three-way stopcock, a rotor, and a septum) was set up, the inside of the apparatus was dried with a heat gun, and then the apparatus was purged with argon. Acetonitrile, 4-t-butylaniline (0.9 mL, 5.91 mmol), and tetradecyl isocyanate (1.4 mL, 5.91 mmol) were placed in this order in the reaction flask, and the mixture was stirred at 90° C. for 2.5 hours. After the completion of the reaction was confirmed by TLC, the resulting solid was collected by filtration, and washed with acetonitrile to obtain a target product as a white solid (yield: 99%, 1.97 g).

$^1$H-NMR (600 MHz, CDCl$_3$) δ=7.35 (2H, d, J=8.9 Hz), 7.17 (2H, d, J=8.9 Hz), 6.04 (1H, s), 4.64 (1H, s), 3.23 (2H, t, J=6.9 Hz), 1.50-1.27 (33H, m), 0.88 (3H, t, J=6.9 Hz).

<Synthesis of Monourea Compound of Formula 26>

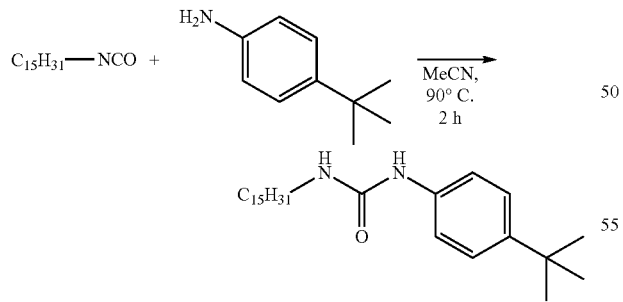

An apparatus (a Schlenk tube, a rotor, and a septum) was set up, the inside of the apparatus was dried with a heat gun, and then the apparatus was purged with argon. Acetonitrile, 4-t-butylaniline (0.1 mL, 0.68 mmol), and pentadecyl isocyanate (0.2 mL, 0.68 mmol) were placed in this order in the Schlenk tube, and the mixture was stirred at 90° C. for 2 hours. After the completion of the reaction was confirmed by TLC, the resulting solid was collected by filtration, and thermally recrystallized from chloroform to obtain a target product as a white solid (yield: 49%, 133 mg).

$^1$H-NMR (600 MHz, DMSO-d$_6$) δ=8.30 (1H, s), 7.27 (2H, d, J=8.6 Hz), 7.21 (2H, d, J=8.6 Hz), 6.07 (1H, s), 3.04 (2H, t, J=6.6 Hz), 1.40-1.24 (35H, m), 0.85 (3H, t, J=7.2 Hz).

<Synthesis of Monourea Compound of Formula 27>

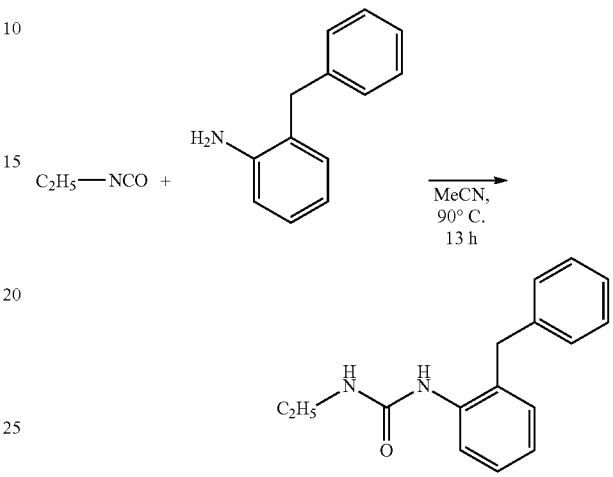

An apparatus (a reaction flask, a three-way stopcock, a rotor, a septum, and a

Dimroth condenser) was set up, the inside of the apparatus was dried with a heat gun, and then the apparatus was purged with argon. 2-Benzylaniline (1.08 g, 5.90 mmol), acetonitrile, and ethyl isocyanate (0.47 mL, 5.90 mmol) were placed in this order in the reaction flask, and the mixture was stirred at 90° C. for 13 hours. After the completion of the reaction was confirmed by TLC, the precipitated solid was collected by filtration. The product was purified by reprecipitation with acetone/hexane to obtain a target product as a white solid (yield: 60%, amount: 0.89 g).

$^1$H NMR (400 MHz, DMSO-d$_6$) δ=7.75 (1H, d, J=8.3 Hz), 7.69 (1H, s), 7.28 (2H, t, J=7.3 Hz), 7.17 (3H, m), 7.13-7.09 (1H, m), 6.99 (1H, dd, J=7.3, 1.5 Hz), 6.91 (1H, td, J=7.3, 1.5 Hz), 6.42 (1H, s), 3.91 (2H, s), 3.08 (2H, t, J=7.0 Hz), 1.04 (3H, t, J=7.1 Hz).

<Synthesis of Monourea Compound of Formula 28>

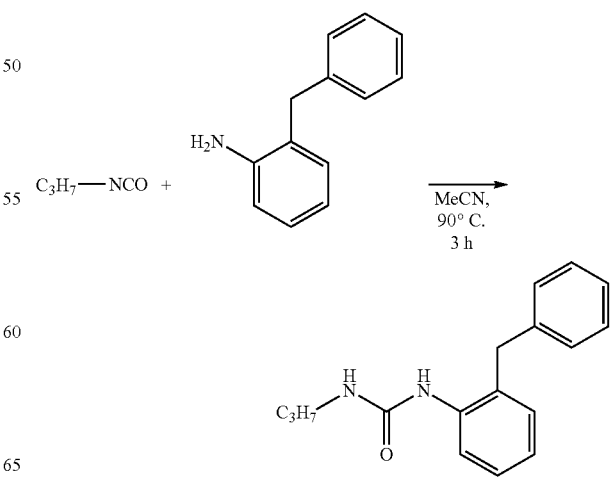

An apparatus (a reaction flask, a three-way stopcock, a rotor, a septum, and a Dimroth condenser) was set up, the inside of the apparatus was dried with a heat gun, and then the apparatus was purged with argon. 2-Benzylaniline (2.05 g, 11.2 mmol), acetonitrile, and propyl isocyanate (1.05 mL, 11.2 mmol) were placed in this order in the reaction flask while cooling with ice, and the mixture was stirred at 90° C. for 3 hours. After the completion of the reaction was confirmed by TLC, the precipitated solid was collected by filtration. The product was purified by reprecipitation with acetone/hexane to obtain a target product as a white solid (yield: 80%, amount: 2.41 g).

$^1$H NMR (400 MHz, DMSO-$d_6$) δ=7.74 (2H, t, J=9.5 Hz), 7.28 (2H, t, J=7.8 Hz), 7.18 (3H, m), 7.11 (1H, t, J=7.8 Hz), 6.99 (1H, d, J=7.8 Hz), 6.90 (1H, t, J=7.6 Hz), 6.47 (1H, s), 3.91 (2H, s), 3.02 (2H, t, J=6.3 Hz), 1.42 (2H, tq, J=6.5, 7.6 Hz), 0.87 (3H, t, J=7.6 Hz).

<Synthesis of Monourea Compound of Formula 29>

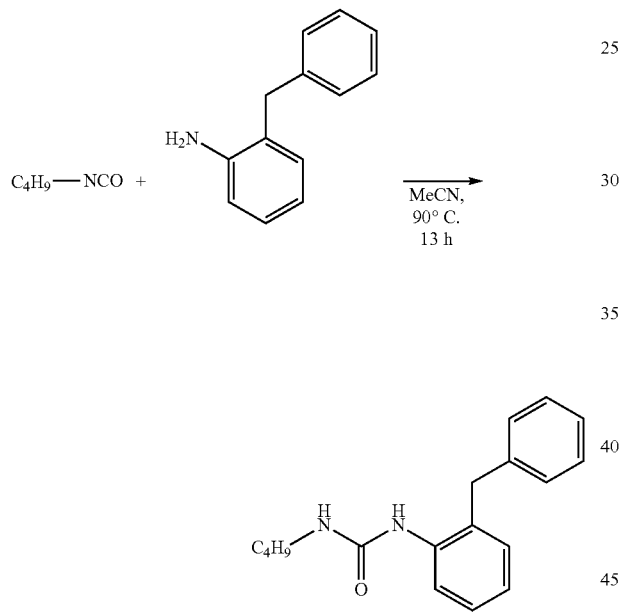

An apparatus (a reaction flask, a three-way stopcock, a rotor, a septum, and a Dimroth condenser) was set up, the inside of the apparatus was dried with a heat gun, and then the apparatus was purged with argon. 2-Benzylaniline (0.97 g, 5.31 mmol), acetonitrile, and n-butyl isocyanate (0.6 mL, 5.31 mmol) were placed in this order in the reaction flask, and the mixture was stirred at 90° C. for 13 hours. After the completion of the reaction was confirmed by TLC, the precipitated solid was collected by filtration. The product was purified by reprecipitation with acetone/hexane to obtain a target product as a white solid (yield: 86%, amount: 1.29 g).

$^1$H NMR (400 MHz, DMSO-$d_6$) δ=7.75 (1H, d, J=8.3 Hz), 7.70 (1H, s), 7.27 (2H, t, J=7.3 Hz), 7.18 (3H, dd, J=7.8, 6.3 Hz), 7.11 (1H, t, J=8.5 Hz), 6.99 (1H, d, J=5.9 Hz), 6.90 (1H, m), 6.43 (1H, s), 3.91 (2H, s), 3.06 (2H, t, J=6.3 Hz), 1.34 (4H, m), 0.89 (3H, t, J=7.3 Hz).

<Synthesis of Monourea Compound of Formula 30>

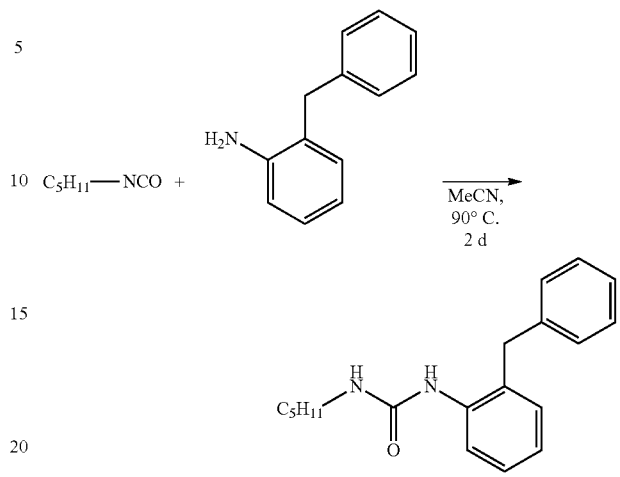

An apparatus (a reaction flask, a three-way stopcock, a rotor, a septum, and a Dimroth condenser) was set up, the inside of the apparatus was dried with a heat gun, and then the apparatus was purged with argon. 2-Benzylaniline (1.85 g, 10.1 mmol), acetonitrile, and pentyl isocyanate (1.30 mL, 10.1 mmol) were placed in this order in the reaction flask while cooling with ice, and the mixture was stirred at 90° C. for 2 days. After the completion of the reaction was confirmed by TLC, the precipitated solid was collected by filtration. The product was purified by reprecipitation with acetone/hexane to obtain a target product as a white solid (yield: 54%, amount: 1.61 g).

$^1$H NMR (400 MHz, DMSO-$d_6$) δ=7.74 (1H, d, J=8.3 Hz), 7.70 (1H, s), 7.27 (2H, dd, J=8.3, 2.1 Hz), 7.18 (3H, m), 7.11 (1H, t, J=6.8 Hz), 7.00 (1H, d, J=7.3 Hz), 6.90 (1H, t, J=7.3 Hz), 6.44 (1H, t, J=5.6 Hz), 3.91 (2H, s), 3.05 (2H, t, J=6.3 Hz), 1.41-1.25 (6H, m), 0.87 (3H, t, J=7.1 Hz).

<Synthesis of Monourea Compound of Formula 31>

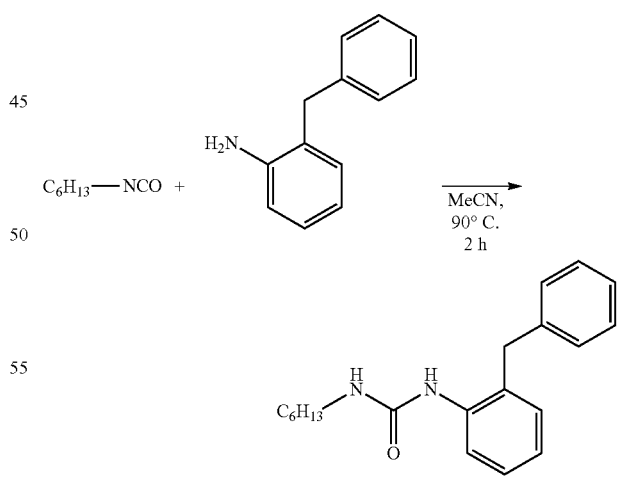

An apparatus (a reaction flask, a three-way stopcock, a rotor, a septum, and a Dimroth condenser) was set up, the inside of the apparatus was dried with a heat gun, and then the apparatus was purged with argon. 2-Benzylaniline (1.77 g, 9.66 mmol), acetonitrile, and hexyl isocyanate (1.40 mL, 9.66 mmol) were placed in this order in the reaction flask while cooling with ice, and the mixture was stirred at 90° C.

for 2 hours. After the completion of the reaction was confirmed by TLC, the precipitated solid was collected by filtration. The product was purified by reprecipitation with acetone/hexane to obtain a target product as a white solid (yield: 91%, amount: 2.74 g).

$^1$H NMR (400 MHz, DMSO-d$_6$) δ=7.73 (2H, t, J=8.5 Hz), 7.27 (2H, t, J=7.6 Hz), 7.18 (3H, m), 7.11 (1H, m), 7.00 (1H, d, J=7.8 Hz), 6.90 (1H, t, J=7.6 Hz), 6.45 (1H, t, J=5.6 Hz), 3.91 (2H, s), 3.05 (2H, t, J=6.5 Hz), 1.40-1.28 (8H, m), 0.87 (3H, t, J=6.6 Hz).

<Synthesis of Monourea Compound of Formula 32>

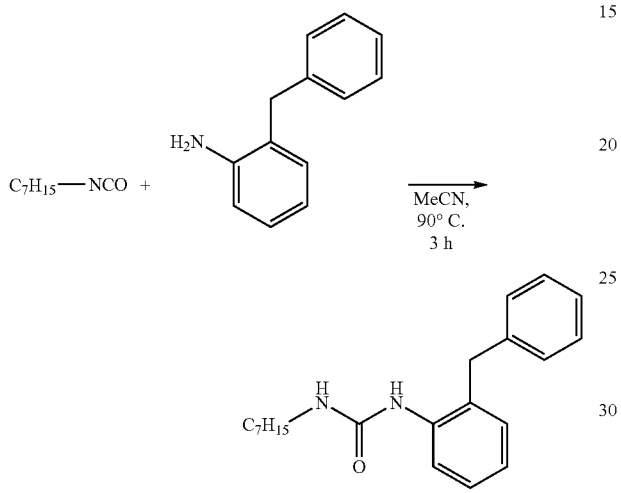

An apparatus (a reaction flask, a three-way stopcock, a rotor, a septum, and a Dimroth condenser) was set up, the inside of the apparatus was dried with a heat gun, and then the apparatus was purged with argon. 2-Benzylaniline (1.70 g, 9.25 mmol), acetonitrile, and heptyl isocyanate (1.48 mL, 9.25 mmol) were placed in this order in the reaction flask while cooling with ice, and the mixture was stirred at 90° C. for 3 hours. After the completion of the reaction was confirmed by TLC, the precipitated solid was collected by filtration. The product was purified by reprecipitation with acetone/hexane to obtain a target product as a white solid (yield: 89%, amount: 2.66 g).

$^1$H NMR (400 MHz, DMSO-d$_6$) δ=7.75 (2H, t, J=6.8 Hz), 7.29 (2H, t, J=7.6 Hz), 7.20 (3H, m), 7.13 (1H, t, J=7.8 Hz), 7.01 (1H, d, J=6.3 Hz), 6.92 (1H, t, J=6.8 Hz), 6.47 (1H, t, J=5.6 Hz), 3.93 (2H, s), 3.07 (2H, t, J=6.3 Hz), 1.42-1.29 (10H, s), 0.88 (3H, t, J=6.8 Hz).

<Synthesis of Monourea Compound of Formula 33>

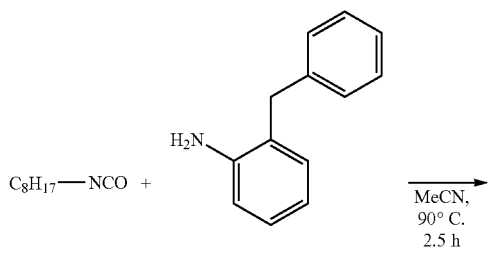

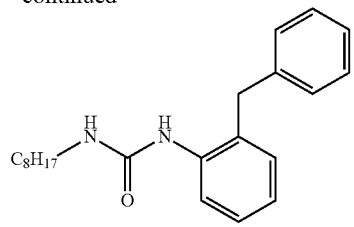

An apparatus (a reaction flask, a three-way stopcock, a rotor, a septum, and a Dimroth condenser) was set up, the inside of the apparatus was dried with a heat gun, and then the apparatus was purged with argon. 2-Benzylaniline (1.8 g, 9.80 mmol), acetonitrile, and octyl isocyanate (1.7 mL, 9.80 mmol) were placed in this order in the reaction flask, and the mixture was stirred at 90° C. for 2.5 hours. After the completion of the reaction was confirmed by TLC, the precipitated solid was collected by filtration, and washed with acetonitrile to obtain a target product as a white solid (yield: 67%, 2.23 g).

$^1$H-NMR (600 MHz, CDCl$_3$) δ=7.41 (2H, d, J=7.6 Hz), 7.28 (2H, m), 7.21 (2H, m), 7.14 (2H, d, J=7.6 Hz), 5.74 (1H, s), 4.32 (1H, t, J=5.2 Hz), 3.99 (2H, s), 3.08 (2H, t, J=6.6 Hz), 1.41-1.36 (2H, m), 1.30-1.24 (10H, m), 0.88 (3H, t, J=7.2 Hz)

<Synthesis of Monourea Compound of Formula 34>

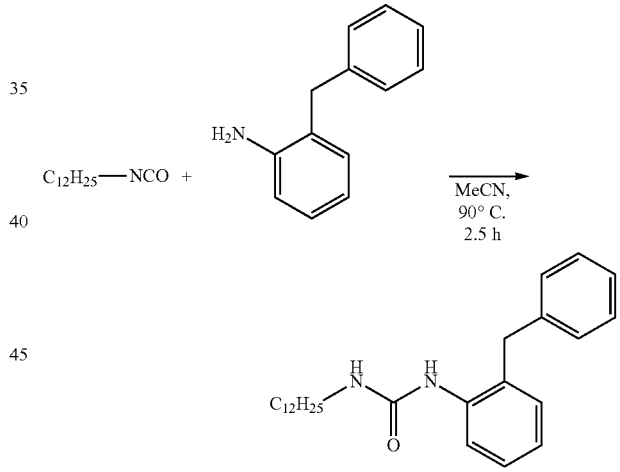

An apparatus (a reaction flask, a three-way stopcock, a rotor, a septum, and a Dimroth condenser) was set up, the inside of the apparatus was dried with a heat gun, and then the apparatus was purged with argon. 2-Benzylaniline (0.93 g, 5.07 mmol), acetonitrile, and dodecyl isocyanate (1.2 mL, 5.07 mmol) were placed in this order in the reaction flask, and the mixture was stirred at 90° C. for 2.5 hours. After the completion of the reaction was confirmed by TLC, the precipitated solid was collected by filtration, and reprecipitated with chloroform/hexane to obtain a target product as a white solid (yield: 72%, 1.43 g).

$^1$H-NMR (600 MHz, CDCl$_3$) δ=7.42 (1H, d, J=7.6 Hz), 7.28 (4H, m), 7.21 (2H, t, J=6.9 Hz), 7.14 (2H, d, J=6.9 Hz), 5.75 (1H, s), 4.32 (1H, t, J=5.8 Hz), 3.99 (2H, s), 3.08 (2H, t, J=6.6 Hz), 1.41-1.28 (20H, t, J=19.9 Hz), 0.88 (3H, t, J=6.9 Hz).

<Synthesis of Monourea Compound of Formula 35>

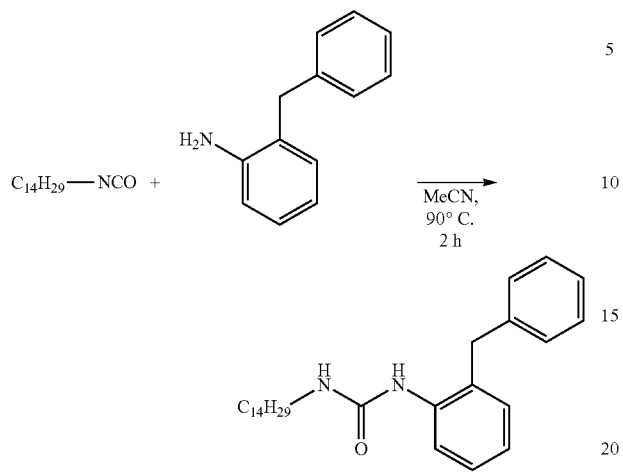

An apparatus (a reaction flask, a three-way stopcock, a rotor, and a septum) was set up, the inside of the apparatus was dried with a heat gun, and then the apparatus was purged with argon. 2-Benzylaniline (0.87 g, 4.73 mmol), acetonitrile, and tetradecyl isocyanate (1.3 mL, 4.73 mmol) were placed in this order in the reaction flask, and the mixture was stirred at 90° C. for 2 hours. After the completion of the reaction was confirmed by TLC, the resulting solid was collected by filtration, and thermally recrystallized from chloroform to obtain a target product as a white solid (yield: 73%, 1.47 g).

$^1$H-NMR (600 MHz, DMSO-$d_6$) δ=7.73 (2H, d, J=9.6 Hz), 7.27 (2H, t, J=7.6 Hz), 7.17 (3H, t, J=6.9 Hz), 7.10 (1H, t, J=7.6 Hz), 6.99 (1H, d, J=6.2 Hz), 6.90 (1H, t, J=7.9 Hz), 6.46 (1H, t, J=5.5 Hz), 3.91 (2H, s), 3.05 (2H, t, J=6.4 Hz), 1.39-1.25 (24H, m), 0.85 (3H, t, J=6.9 Hz).

<Synthesis of Monourea Compound of Formula 36>

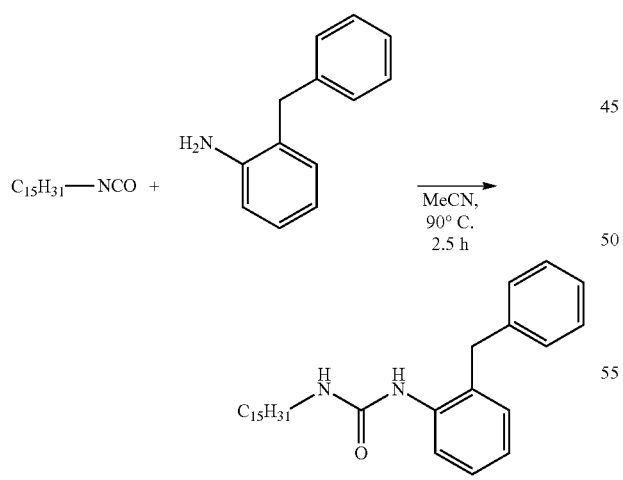

An apparatus (a Schlenk tube, a rotor, and a septum) was set up, the inside of the apparatus was dried with a heat gun, and then the apparatus was purged with argon. Acetonitrile, 2-benzylaniline (125 mg, 0.68 mmol), and pentadecyl isocyanate (0.2 mL, 0.68 mmol) were placed in this order in the Schlenk tube, and the mixture was stirred at 90° C. for 2.5 hours. After the completion of the reaction was confirmed by TLC, the resulting solid was collected by filtration, and washed with acetonitrile to obtain a target product as a white solid (yield: 87%, 258 g).

$^1$H-NMR (600 MHz, DMSO-$d_6$) δ: 7.74 (1H, d, J=8.2 Hz), 7.71 (1H, s), 7.27 (2H, t, J=7.9 Hz), 7.18 (3H, t, J=7.2 Hz), 7.11 (1H, t, J=6.9 Hz), 6.99 (1H, d, J=6.2 Hz), 6.90 (1H, t, J=7.9 Hz), 6.45 (1H, t, J=5.5 Hz), 3.91 (2H, s), 3.05 (2H, t, J=6.6 Hz), 1.39-1.25 (26H, m), 0.85 (3H, t, J=6.9 Hz).

<Synthesis of Monourea Compound of Formula 37>

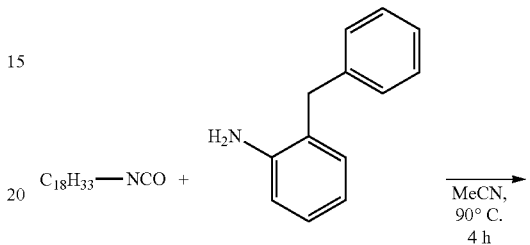

An apparatus (a reaction flask, a three-way stopcock, a rotor, a septum, and a Dimroth condenser) was set up, the inside of the apparatus was dried with a heat gun, and then the apparatus was purged with argon. 2-Benzylaniline (0.81 g, 4.44 mmol), acetonitrile, and hexadecyl isocyanate (1.4 mL, 4.44 mmol) were placed in this order in the reaction flask, and the mixture was stirred at 90° C. for 4 hours. After the completion of the reaction was confirmed by TLC, the precipitated solid was collected by filtration, and reprecipitated with chloroform/hexane to obtain a target product as a white solid (yield: 51%, 1.02 g).

$^1$H-NMR (600 MHz, DMSO-$d_6$) δ=7.73 (2H, d, J=10.3 Hz), 7.27 (2H, t, J=7.9 Hz), 7.17 (3H, t, J=7.6 Hz), 7.10 (1H, t, J=7.6 Hz), 6.99 (1H, d, J=6.2 Hz), 6.90 (1H, t, J=6.9 Hz), 6.45 (1H, t, J=5.5 Hz), 3.91 (2H, s), 3.05 (2H, t, J=6.4 Hz), 1.39-1.25 (28H, m), 0.85 (3H, t, J=7.2 Hz).

<Synthesis of Monourea Compound of Formula 38>

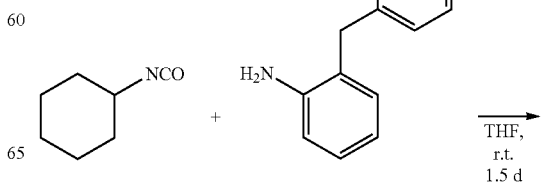

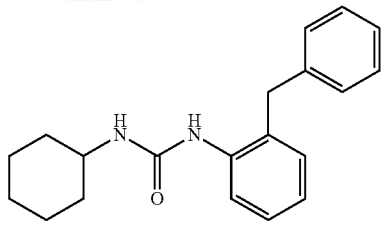

An apparatus (a reaction flask, a three-way stopcock, a rotor, and a septum) was set up, the inside of the apparatus was dried with a heat gun, and then the apparatus was purged with argon. 2-Benzylaniline (1.2 g, 6.48 mmol), tetrahydrofuran (THF), and cyclohexyl isocyanate (0.8 mL, 6.48 mmol) were placed in this order in the reaction flask, and the mixture was stirred at room temperature for 1.5 days. After the completion of the reaction was confirmed by TLC, the solvent was distilled under reduced pressure, and the resulting solid was washed with THF to obtain a target product as a white solid (yield: 65%, 1.30 g).

$^1$H-NMR (600 MHz, CDCl$_3$) δ=7.43 (1H, d, J=7.6 Hz), 7.30 (3H, m), 7.26 (1H, s), 7.23-7.19 (2H, m), 7.15 (2H, d, J=7.6 Hz), 5.73 (1H, s), 4.25 (1H, s), 4.00 (2H, s), 3.52 (1H, s), 1.86 (2H, dd, J=12.7, 3.1 Hz), 1.66-1.63 (2H, m), 1.60 (1H, dd, J=7.9, 3.8 Hz), 1.36-1.28 (2H, m), 1.10 (1H, m), 1.01 (2H, m).

<Synthesis of Monourea Compound of Formula 39>

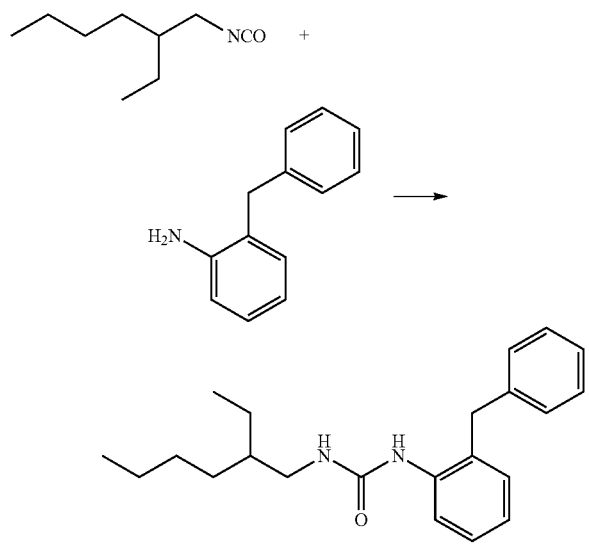

An apparatus (a reaction flask, a three-way stopcock, a rotor, a septum, and a Dimroth condenser) was set up, the inside of the apparatus was dried with a heat gun, and then the apparatus was purged with argon. 2-Benzylaniline (1.08 g, 5.90 mmol), acetonitrile, and 2-ethylhexyl isocyanate (1.1 mL, 5.90 mmol) were placed in this order in the reaction flask while cooling with ice, and the mixture was stirred at 90° C. for 2 hours. After the completion of the reaction was confirmed by TLC, the precipitated solid was collected by filtration. The product was purified by washing with acetonitrile to obtain a target product as a white solid (yield: 56%, 1.12 g).

$^1$H NMR (400 MHz, DMSO-d$_6$) δ=7.75 (2H, d, J=7.8 Hz), 7.27 (2H, t, J=7.3 Hz), 7.23-7.15 (3H, m), 7.11 (1H, t, J=7.6 Hz), 7.00 (1H, d, J=7.8 Hz), 6.90 (1H, t, J=7.3 Hz), 6.42 (1H, t, J=5.6 Hz), 3.91 (2H, s), 3.03 (2H, m), 1.40-1.16 (9H, m), 0.89-0.83 (6H, m).

Example 2: Gel-Forming Abilities of Gelators (1)

Figure 11:
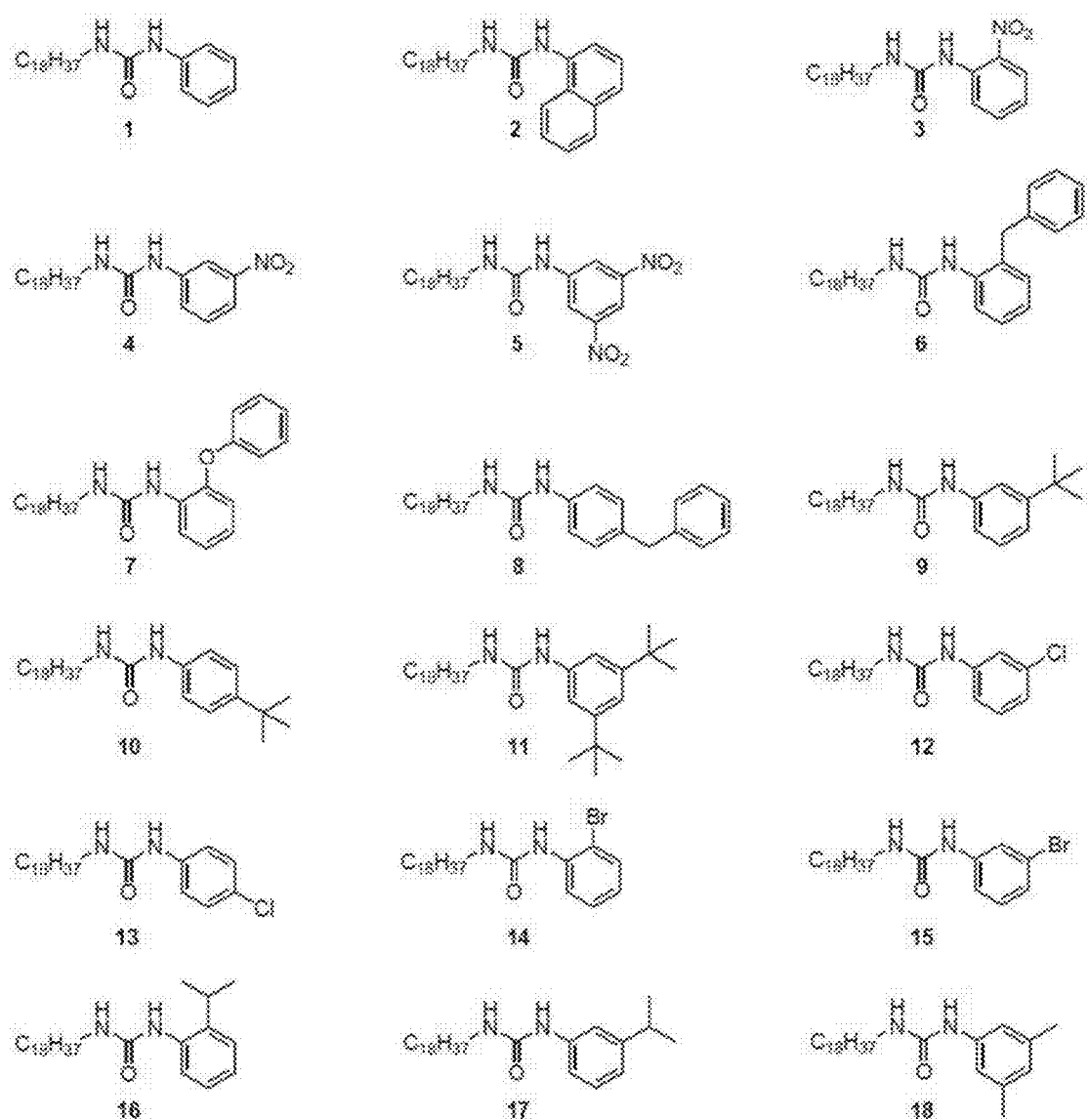
FIG. 11 is a diagram showing structural formulae of compounds of formulae 1 to 18 synthesized in Example 1.
Figure 12:
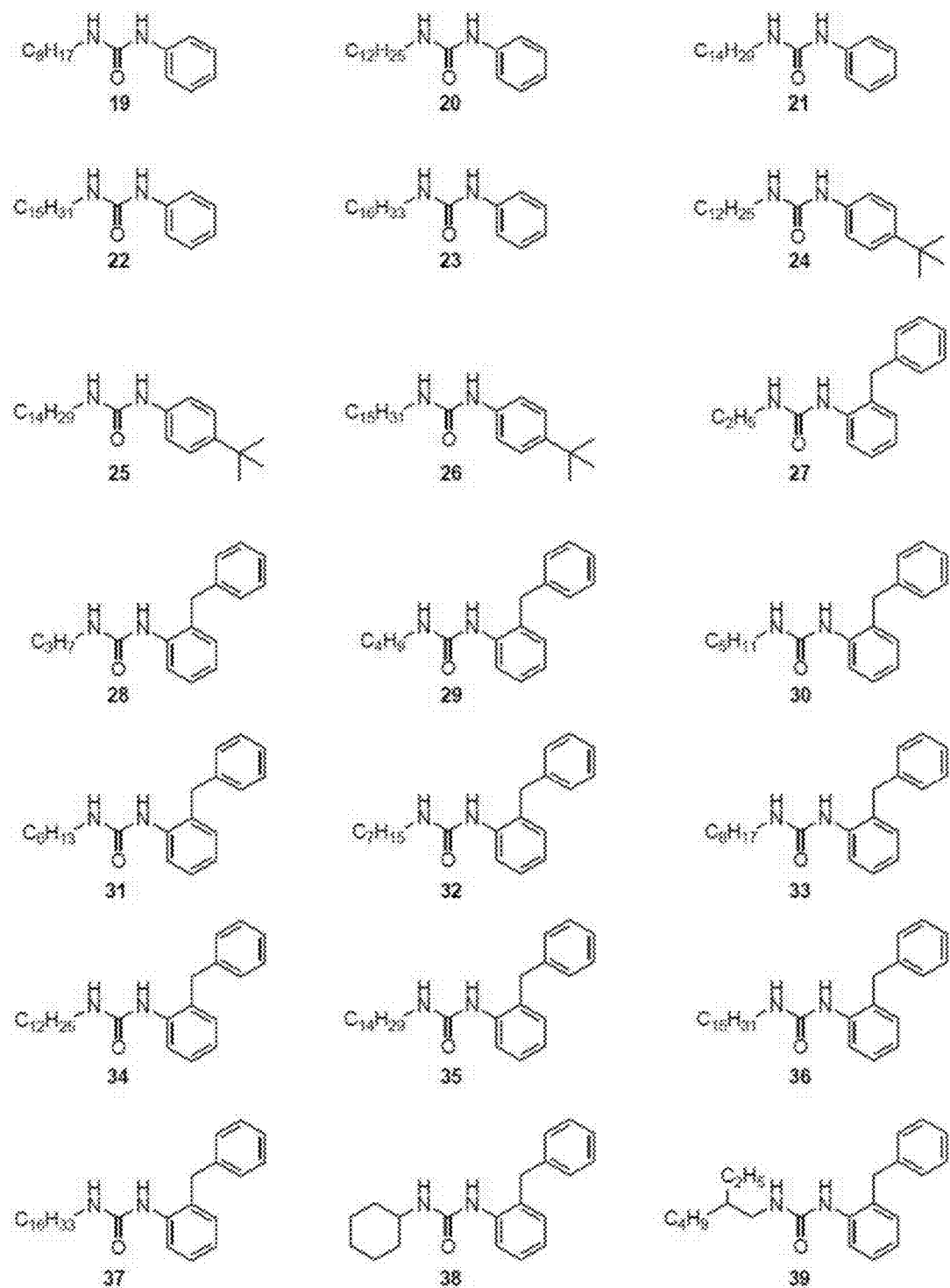
FIG. 12 is a diagram showing structural formulae of compounds of formulae 19 to 39 synthesized in Example 1.

The thirty nine monourea compounds synthesized in Example 1 were used as gelators, and their gel-forming abilities were evaluated with various solvents (liquid paraffin, squalane, isopropyl myristate, SH245, and a 70% aqueous solution of ethanol). FIGS. 11 and 12 show the structural formulae of the thirty nine monourea compounds synthesized in Example 1.

The gelation test was performed as follows: A gelator (5.0 mg) was weighed out into a 2.0-mL screw cap sample tube, each of the various solvents (500 μL) was added thereto, and the mixture was heated on a hot plate at 120° C. to dissolve the gelator. The solution was subsequently allowed to stand overnight at room temperature, and the formation of a gel was observed. FIGS. 1 to 9 show the gelation behavior in the sample tubes after being allowed to stand in the gelation tests using the compounds of formulae 1 to 18 as gelators.

"Gelation" was determined as a state in which the solution lost its flowability after being allowed to cool, and did not flow down even when the sample tube was inverted.

The signs used in the table show gel states (the same applies to the other tables hereinbelow); a transparent gel was evaluated as "G", a partially gelled product was evaluated as "PG", a soft gel was evaluated as "SG", a sol was evaluated as "S", and a suspension was evaluated as "SUS". A product not evaluated was denoted as "nd". The evaluation results are shown in [Table 1-1] and [Table 1-2].

Furthermore, in this test, for the cases where transparent gels were obtained, the gelation test was performed in the same manner by changing the amount of the gelator added, and the minimum amount of the gelator (minimum gelation concentration) required for gelation of each of the various solvents was determined. [Table 1-1] and [Table 1-2] show minimum gelation concentrations within parentheses (w/v %).

TABLE 1-1

| No. | Liquid Paraffin | Squalane | Isopropyl Myristate | SH245 | 70% Ethanol |
|---|---|---|---|---|---|
| 1 | G (0.1) | G (0.25) | G (0.5) | SUS | G (1.0) |
| 2 | G (0.25) | G (0.25) | PG | SUS | SUS |
| 3 | G | G | PG | nd | nd |
| 4 | G (0.5) | S | SUS | SUS | G (1.0) |
| 5 | G (1.0) | S | SUS | SUS | SUS |
| 6 | G (0.5) | S | G (0.5) | G (0.75) | G (0.25) |
| 7 | G (0.25) | G (1.0) | SUS | SUS | SUS |
| 8 | G (0.25) | S | SUS | SUS | SUS |
| 9 | G (0.25) | S | G (1.0) | SUS | SUS |
| 10 | G (1.0) | G (1.0) | G (1.0) | SUS | SUS |
| 11 | S | S | G (0.75) | SUS | SUS |
| 12 | G (0.25) | PG | S | SUS | SUS |
| 13 | G (0.5) | S | SUS | SUS | SUS |

TABLE 1-1-continued

| No. | Liquid Paraffin | Squalane | Isopropyl Myristate | SH245 | 70% Ethanol |
|---|---|---|---|---|---|
| 14 | G (0.25) | G (0.5) | G (1.0) | G (0.5) | SUS |
| 15 | G (0.5) | S | SUS | SUS | G (0.5) |
| 16 | G (0.1) | S | PG | G (0.75) | SUS |
| 17 | G (0.1) | G (0.1) | PG | SUS | SUS |
| 18 | G (0.05) | G (0.5) | S | SUS | SUS |

TABLE 1-2

| No. | Liquid Paraffin | Squalane | Isopropyl Myristate | SH245 | 70% Ethanol |
|---|---|---|---|---|---|
| 19 | G (0.5) | SUS | PG | SUS | S |
| 20 | G (0.05) | S | SUS | S | S |
| 21 | G (0.15) | S | SUS | SUS | G (1.0) |
| 22 | G (0.25) | G (0.25) | S | SUS | S |
| 23 | G (0.05) | S | PG | G (1.0) | G (1.0) |
| 24 | SUS | SUS | SUS | G (0.25) | S |
| 25 | G (1.0) | S | PG | S | S |
| 26 | G (0.1) | S | PG | S | S |
| 27 | G (0.25) | G (0.05) | G | G (0.05) | SUS |
| 28 | G (0.05) | G (0.1) | G (0.5) | G (0.25) | SUS |
| 29 | G (0.25) | G (0.05) | G (0.75) | G (0.05) | SUS |
| 30 | G (0.05) | G (0.05) | G (0.75) | G (1.5) | SUS |
| 31 | G (0.03) | G (0.1) | G (0.75) | G (0.25) | SUS |
| 32 | G (0.05) | G (0.05) | G (0.75) | G (0.25) | G (0.5) |
| 33 | G (0.05) | G (0.05) | PG | G (0.05) | G (0.25) |
| 34 | G (0.02) | G (0.1) | G (1.0) | G (0.05) | G (0.1) |
| 35 | G (0.05) | G (0.5) | G (0.75) | G (0.4) | G (0.25) |
| 36 | G (0.02) | G (0.1) | G (1.0) | G (0.25) | G (0.25) |
| 37 | G (0.1) | S | G (1.0) | G (0.5) | G (0.25) |
| 38 | G (0.25) | SUS | SUS | SUS | SUS |
| 39 | G (0.05) | G (0.1) | G (0.1) | S | PG |

Example 3: Gel-Forming Abilities of Gelators (2)

The monourea compounds of formulae 6, 29, 31, 32, 33, 34, 35, and 36 synthesized in Example 1 were used as gelators, and their gel-forming abilities were evaluated with various hydrophobic organic solvents (methylene chloride (dichloromethane), chloroform, toluene, hexane, and ethyl acetate). The hydrophobic organic solvents used herein were not admixed with water at any proportions.

The gelation test was performed following the same procedures as described in [Example 2], i.e., a gelator (5.0 mg) was weighed out into a 2.0-mL screw cap sample tube, each of the various hydrophobic organic solvents (500 µL) was added thereto, and the mixture was heated on a hot plate at 120° C. to dissolve the gelator. The solution was subsequently allowed to stand overnight at room temperature, and the formation of a gel was observed. "Gelation" was determined as a state in which the solution lost its flowability after being allowed to cool, and did not flow down even when the sample tube was inverted. A transparent gel was evaluated as "G", and a suspension was evaluated as "SUS". The results are shown in [Table 2].

Furthermore, as in Example 2, for the cases where transparent gels were obtained, the gelation test was performed by changing the amount of the gelator added, and the minimum amount of the gelator (minimum gelation concentration) required for gelation of each of the various solvents was determined. [Table 2] shows minimum gelation concentrations within parentheses (w/v %).

TABLE 2

| No. | Ethyl Acetate | Methylene Chloride | Chloroform | Toluene | n-Hexane |
|---|---|---|---|---|---|
| 6 | — | SUS | SUS | G (0.75) | G (0.75) |
| 29 | SUS | SUS | SUS | SUS | G (0.5) |
| 31 | SUS | SUS | SUS | SUS | G (1.25) |
| 32 | SUS | SUS | SUS | SUS | G (0.25) |
| 33 | SUS | SUS | SUS | SUS | G (1.0) |
| 34 | SUS | SUS | SUS | G (1.0) | G (1.0) |
| 35 | SUS | SUS | SUS | SUS | G (1.0) |
| 36 | SUS | SUS | SUS | SUS | G (1.0) |

As shown in [Table 2], the eight monourea compounds used did not form gels with ethyl acetate, methylene chloride, and chloroform; however, the monourea compounds of formulae 6 and 34 were confirmed to form transparent gels with toluene, and all the eight monourea compounds used were confirmed to form transparent gels with n-hexane.

Example 4: Gel-Forming Abilities of Gelators (3)

The monourea compounds of formulae 1, 4, 6, 15, 21, 23, 27, 32, 33, 34, 35, 36, and 37 synthesized in Example 1 were used as gelators, and their gel-forming abilities were evaluated with various hydrophilic organic solvents (dimethylsulfoxide (DMSO) and acetonitrile) and hydrophilic organic solutions (mixed solvents of water and hydrophilic organic solvents: 70% aqueous solution of ethanol and 20% aqueous solution of 1,3-butanediol). The hydrophilic organic solvents used herein were admixed with water at any proportions, as described above.

The gelation test was performed following the same procedures as described in [Example 2], i.e., a gelator (5.0 mg) was weighed out into a 2.0-mL screw cap sample tube, each of the various hydrophilic organic solvents or hydrophilic organic solutions (500 µL) was added thereto, and the mixture was heated on a hot plate at 120° C. to dissolve the gelator. The solution was subsequently allowed to stand overnight at room temperature, and the formation of a gel was observed. "Gelation" was determined as a state in which the solution lost its flowability after being allowed to cool, and did not flow down even when the sample tube was inverted. A transparent gel was evaluated as "G", a sol was evaluated as "S", and a suspension was evaluated as "SUS". The results are shown in [Table 3].

Furthermore, as in Example 2, for the cases where transparent gels were obtained, the gelation test was performed by changing the amount of the gelator added, and the minimum amount of the gelator (minimum gelation concentration) required for gelation of each of the various solvents/solutions was determined. [Table 3] shows minimum gelation concentrations within parentheses (w/v %).

TABLE 3

| No. | DMSO | Acetonitrile | 70% Ethanol (Same as Above) | 20% 1,3-Butanediol |
|---|---|---|---|---|
| 1 | — | — | G (1.0) | SUS |
| 4 | — | — | G (1.0) | SUS |
| 6 | G (0.5) | G (0.5) | G (0.25) | SUS |
| 15 | — | — | G (0.5) | SUS |
| 21 | — | — | G (1.0) | S |
| 23 | — | — | G (1.0) | SUS |
| 27 | S | SUS | SUS | G (0.25) |
| 32 | SUS | SUS | G (0.5) | SUS |
| 33 | SUS | SUS | G (0.25) | SUS |
| 34 | SUS | G (0.75) | G (0.1) | SUS |
| 35 | SUS | SUS | G (0.25) | SUS |
| 36 | G (0.75) | G (0.25) | G (0.25) | SUS |
| 37 | G (1.25) | G (1.0) | G (0.25) | SUS |

Example 5: Gel-Forming Abilities of Gelators (4)

The monourea compounds of formulae 1, 3, 6, 32, 33, 34, 35, 36, and 37 synthesized in Example 1 were used as gelators, and their gel-forming abilities were evaluated with various ionic liquids. The following six ionic liquids were used:

[Me$_3$PrN][Tf$_2$N]: trimethylpropylammonium bis(trifluoromethylsulfonyl)imide

[EtMeIm][AcO]: 1-ethyl-3-methylimidazolium acetate

[EtMeIm][TfO]: 1-ethyl-3-methylimidazolium trifluoromethanesulfonate

[EtMeIm][Tf$_2$N]: 1-ethyl-3-methylimidazolium bis[trifluoromethylsulfonyl]imide

[BuMeIm][BF$_4$]: 1-butyl-3-methylimidazolium tetrafluoroborate

Figure 10:
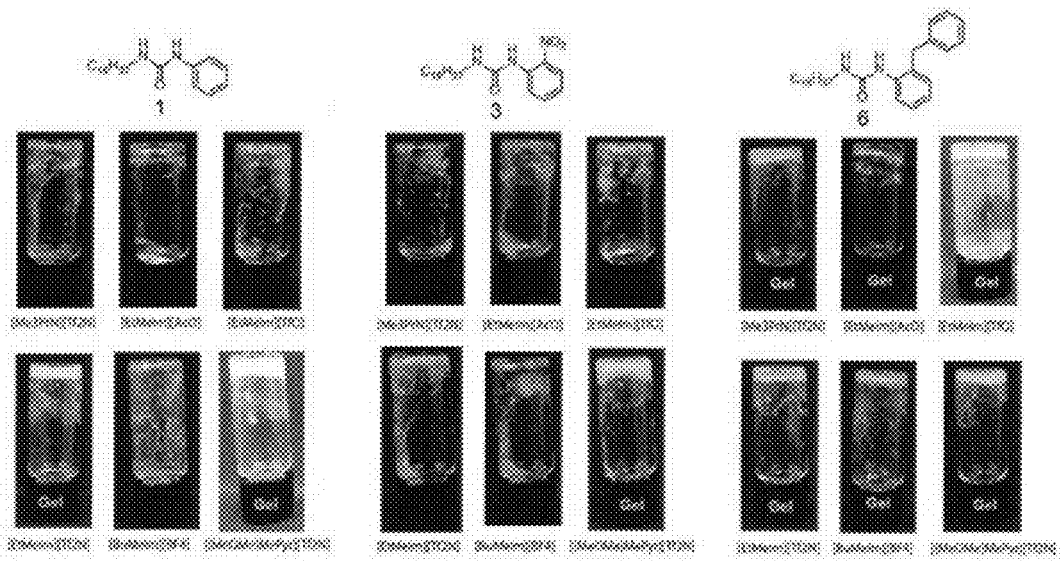
FIG. 10 is a photograph showing gelation behavior of a compound of formula 1, 3, or 6 in ionic liquids in Example 5.

[(MeOMe)MePyr][Tf$_2$N]: N-methoxymethyl-N-methylpyrrolidinium bis(trifluoromethylsulfonyl)imide The gelation test was performed following the same procedures as described in [Example 2], i.e., a gelator (5.0 mg) was weighed out into a 2.0-mL screw cap sample tube, each of the various ionic liquids (500 μL) was added thereto, and the mixture was heated on a hot plate at 120° C. to dissolve the gelator. The solution was subsequently allowed to stand overnight at room temperature, and the formation of a gel was observed. The results are shown in [Table 4]. Moreover, FIG. 10 shows the gelation behavior of some gelators (gelators: monourea compounds of formulae 1, 3, and 6) in sample tubes after being allowed to stand.

Furthermore, regarding the examples using the monourea compounds of formulae 32, 33, 34, 35, 36, and 37 as gelators, the gelation test was performed for cases where transparent gels were obtained, as in Example 2, by changing the amount of the gelator added, and the minimum amount of the gelator (minimum gelation concentration) required for gelation of each of the various ionic liquids was determined. [Table 4] shows minimum gelation concentrations within parentheses (w/v %).

TABLE 4

| No. | [Me$_3$PrN][Tf$_2$N] | [EtMeIm][AcO] | [EtMeIm][TfO] | [EtMeIm][Tf$_2$N] | [BuMeIm][BF$_4$] | [(MeOMe)MePyr][Tf$_2$N] |
|---|---|---|---|---|---|---|
| 1 | — | — | — | G | — | G |
| 3 | — | — | — | — | — | G |
| 6 | G | G | G | G | G | G |
| 32 | G (1.0) | — | — | G (1.0) | — | — |
| 33 | G (1.0) | — | — | G (1.0) | G (1.0) | — |
| 34 | G (0.25) | — | — | G (0.25) | G (0.1) | — |
| 35 | G (0.5) | — | — | G (0.25) | G (0.05) | — |
| 36 | G (0.25) | — | — | G (0.1) | G (0.05) | — |
| 37 | G (0.25) | — | — | G (0.25) | G (0.05) | — |

As shown in Examples 2 to 5, the gelators of the present invention were confirmed to form gels with hydrophobic organic solvents, hydrophilic organic solvents, hydrophilic organic solutions, or ionic liquids.

The invention claimed is:

1. A gelator comprising a compound of formula (1):

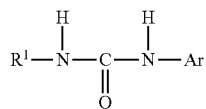

wherein
R$^1$ is a linear alkyl group having a carbon atom number of 14 to 20; and
Ar is a phenyl group substituted with a benzyl group.

2. A gel comprising the gelator according to claim 1, and a hydrophobic organic solvent, a hydrophilic organic solvent, a hydrophilic organic solution, or an ionic liquid.

3. The gel according to claim 2, wherein the hydrophobic organic solvent is at least one selected from the group consisting of a vegetable oil, an ester, a silicone oil, and a hydrocarbon.

4. The gel according to claim 2, wherein the hydrophilic organic solvent is at least one selected from the group consisting of methanol, ethanol, 2-propanol, i-butanol, pentanol, hexanol, 1-octanol, isooctanol, acetone, cyclohexanone, acetonitrile, dioxane, glycerol, butanediol, propylene glycol, ethylene glycol, and dimethylsulfoxide.

5. The gel according to claim 2, wherein
the hydrophilic organic solution is a mixed solvent of a hydrophilic organic solvent and water, and
the hydrophilic organic solvent is at least one selected from the group consisting of methanol, ethanol, 2-propanol, i-butanol, pentanol, hexanol, 1-octanol, isooctanol, acetone, cyclohexanone, acetonitrile, dioxane, glycerol, butanediol, propylene glycol, ethylene glycol, and dimethylsulfoxide.

6. The gel according to claim 2, wherein the ionic liquid comprises a combination of a cationic species selected from the group consisting of imidazolium, pyridinium, piperidinium, pyrrolidinium, phosphonium, ammonium, and sulfonium, and an anionic species selected from the group consisting of a halogen, a carboxylate, a sulfate, a sulfonate, a thiocyanate, a nitrate, an aluminate, a borate, a phosphate, an amide, an antimonate, an imide, and a methide.

* * * * *